United States Patent
Chattaraj et al.

(10) Patent No.: US 9,949,933 B2
(45) Date of Patent: *Apr. 24, 2018

(54) FENOFIBRATE FORMULATION

(71) Applicant: MYLAN INC., Morgantown, WV (US)

(72) Inventors: Sarat C. Chattaraj, Morgantown, WV (US); Glenn Allen Redelman, Morgantown, WV (US); Andrew Alan Shaw, Morgantown, WV (US)

(73) Assignee: Mylan Inc., Canonsburg, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/224,177

(22) Filed: Jul. 29, 2016

(65) Prior Publication Data

US 2016/0331694 A1  Nov. 17, 2016

Related U.S. Application Data

(63) Continuation of application No. 14/390,556, filed as application No. PCT/US2012/061486 on Oct. 23, (Continued)

(51) Int. Cl.
*A61K 9/50* (2006.01)
*A61K 9/14* (2006.01)
(Continued)

(52) U.S. Cl.
CPC .............. *A61K 9/5047* (2013.01); *A61K 9/14* (2013.01); *A61K 9/5078* (2013.01); (Continued)

(58) Field of Classification Search
None
See application file for complete search history.

(56) References Cited

U.S. PATENT DOCUMENTS

| 6,696,084 B2 | 2/2004 | Pace et al. |
| 7,037,529 B2 | 5/2006 | Stamm et al. |

(Continued)

FOREIGN PATENT DOCUMENTS

| WO | 2008014175 A2 | 1/2008 |
| WO | 2008075320 A2 | 6/2008 |

OTHER PUBLICATIONS

"International Search Report for PCT/US2012/061486 dated Dec. 28, 2012".

(Continued)

*Primary Examiner* — Aradhana Sasan

(57) ABSTRACT

Various fenofibrate dosage forms contain a plurality of beads or particles, where the beads or particles include a pharmaceutical composition comprising fenofibrate; from 0.3% to 10% by weight of the beads or particles of a surfactant; and from about 5% to about 15% by weight of the beads or particles of a water soluble or water dispersible cellulosic binder. The mass ratio of the drug to the binder in the dosage form is between about 3.5:1 and 4.5:1; and the dosage form produces a first Cmax in vivo that is between about 10% and about 50% higher than a comparative Cmax produced by a comparative dosage form. The comparative dosage form comprises the drug and the binder in a ratio of between about 5:1 and 15:1.

The dosage form may contain a plurality of beads or particles, each of the beads or particles including a pharmaceutical composition containing from about 20% to about 55% by weight of fenofibrate; from 0.3% to 10% by weight of a surfactant; and from about 5% to about 15% by weight of a water soluble or water dispersible cellulosic binder.

22 Claims, 4 Drawing Sheets

Related U.S. Application Data 2012, now Pat. No. 9,439,860, which is a continuation-in-part of application No. 13/531,955, filed on Jun. 25, 2012, now Pat. No. 8,722,083.

(51) Int. Cl.
*A61K 45/06* (2006.01)
*A61K 31/216* (2006.01)

(52) U.S. Cl.
CPC .......... *A61K 9/5084* (2013.01); *A61K 31/216* (2013.01); *A61K 45/06* (2013.01)

(56) References Cited

U.S. PATENT DOCUMENTS

| | | | |
|---|---|---|---|
| 7,041,319 | B2 | 5/2006 | Stamm et al. |
| 7,863,331 | B2 | 1/2011 | Criere et al. |
| 8,722,083 | B2 | 5/2014 | Chattaraj et al. |
| 9,439,860 | B2 * | 9/2016 | Chattaraj ............. A61K 9/5047 |
| 2003/0077297 | A1 | 4/2003 | Chen |
| 2004/0137055 | A1 | 7/2004 | Criere et al. |
| 2008/0063726 | A1 | 3/2008 | Stamm et al. |
| 2008/0241070 | A1 | 10/2008 | Ryde et al. |
| 2009/0028941 | A1 | 1/2009 | Cowles |
| 2009/0035379 | A1 | 2/2009 | Stamm et al. |
| 2010/0166857 | A1 | 7/2010 | Yan et al. |
| 2011/0217369 | A1 | 9/2011 | Amit et al. |
| 2011/0311619 | A1 | 12/2011 | Herry |
| 2011/0311625 | A1 | 12/2011 | Doddaveerappa et al. |

OTHER PUBLICATIONS

Siepman, et al., "Hydrophilic matrices for Controlled Drug Delivery: An Improved Mathematical Model to Predict the REsultring Drug Release Kinetics (the "Sequential layer" Model)", Pharmaceutical Research, vol. 17, No. 10, 2000, 190-1298.

Sornay, et al., "Antilipidemic Drugs", Arznelm Forsh (Drug Res.) 26, Nr. 5 (1976), 885-889.

EP Search Report for EP Application No. 12 87 9875 dated Nov. 12, 2015.

* cited by examiner

FENOFIBRATE FORMULATION

CROSS-REFERENCE TO RELATED APPLICATIONS

This is Continuation of application Ser. No. 14/390,556, filed Oct. 3, 2014, which is a National Stage application based on International Application PCT/US2012/061486, filed Oct. 23, 2012, which is a Continuation-in-Part of U.S. application Ser. No. 13/531,955, filed Jun. 25, 2012. The entire disclosure of each prior application is hereby incorporated by reference in its entirety.

BACKGROUND

Field

This invention relates generally to immediate release fenofibrate dosage forms.

Description of Related Art

Fenofibrate is an active principle which is very poorly soluble in water, and the absorption of fenofibrate in the digestive tract is limited. An increase in its solubility leads to better digestive absorption. Various approaches have been explored in order to increase the solubility of fenofibrate, including micronization of the active principle, addition of a surfactant, and comicronization of fenofibrate with a surfactant.

Fenofibrate is freely soluble in methanol and acetonitrile, and insoluble in water. Having no ionizable group, fenofibrate solubility is not influenced by changes in medium pH. However, the aqueous solubility of Fenofibrate can be improved in the presence of surfactants. As the concentration of the surfactant sodium lauryl sulfate, for example, increases from 0.0 M to 0.1 M, fenofibrate solubility increases from 0.8 mg/L to 910.8 mg/L.

There are various lipid regulating agents, such as atorvastatin, cerivastatin, ezetimibe, fluvastatin, lovastatin, pitavastatin, pravastatin, probucol, rosuvastatin, simvastatin and fibrates. The fibrates are a group of drugs which are known as hypolipidaemic agents. They include benzafibrate, clofibrate, ciprofibrate, fenofibrate and gemfibrozil. The fibrates have the beneficial effect of lowering cholesterol levels in the blood and hence reducing the risk of coronary heart disease.

Fenofibrate is a fibric acid derivative that has been marketed since the mid 1970's (1998 in the United States) as a lipid regulating drug. The chemical name of fenofibrate is 2-[4-(4-chlorobenzoyl) phenoxy]-2-methyl-propionic acid, 1-methyl ester. It has a molecular formula $C_{20}H_{21}O_4Cl$ and a molecular weight of 360.83. The melting point of fenofibrate is 79° C. to 82° C. Fenofibrate is a white solid that is stable under ordinary conditions. Fenofibrate is absorbed as fenofibric acid, which is responsible for the pharmacological activity.

Fenofibrate has an extremely low solubility in water of around 6 micrograms/ml. This can adversely affect absorption of drugs of the drug substance in vivo, leading to poor bioavailability. Consequently higher amounts of the drug substance are required to achieve the desired blood levels. The poor solubility of the fenofibrate also restricts the options available for formulating the drug substance.

The standards for bioavailability and/or bioequivalence depend on several natural log transformed parameters associated with the rate and extent of absorption. Specifically, the rate and extent of absorption is measured by the parameters AUCL, AUCI, and Cmax. The parameter AUCL is the area under the plasma concentration-time curve from time zero to time t, where t is the last time point with measurable concentration for individual formulation. The parameter AUCI is the area under the plasma concentration-time curve from time zero to time infinity. Additionally, Cmax, sometimes referred to as Cpeak, is the maximum plasma concentration of the drug. For two products to be bioequivalent, the 90% confidence interval of the relative mean Cmax, AUCL, and AUCI of the test product to reference product should be within 80% to 125%.

Many methods have been used to enhance dissolution rates of poorly water-soluble or insoluble drugs in general, and fenofibrate in particular. Such methods include micronization of fenofibrate, microcrystallization of fenofibrate, preparation solid fenofibrate dispersions, and coprecipitation of fenofibrate with inert, water-soluble compounds as carriers. Other methods include grinding fenofibrate with an inert water-insoluble compound, so that fenofibrate is adsorbed onto the inert compound.

European Patent EP 256933 teaches fenofibrate granules which contain micronized fenofibrate. The crystalline fenofibrate particles are less than 50 microns in size. The micronized fenofibrate may be granulated with various types of binder polymers, such as polyvinylpyrrolidone, methacrylic polymers, cellulose derivatives, and polyethylene glycols, where an organic solvent is used for the granulation.

European Patent EP 330532 teaches improving the bioavailability of fenofibrate by comicronizing fenofibrate with a solid wetting agent or surfactant, such as sodium lauryl sulfate. The comicronizate is then granulated by wet granulation in order to improve the flow capacities of the powder and to facilitate filling into gelatin capsules. The comicronizate may be granulated with excipients such as lactose, starch, polyvinyl pyrrolidone and/or magnesium stearate. A formulation of the composition described in EP 330532 was compared to the formulation described in patent EP 256933, discussed above, and found to show a statistically significant increase in bioavailability vs. the formulation of EP 256933. Specifically, 67 mg fenofibrate in the formulation of EP 330532 gave the same absorption in vivo as 100 mg fenofibrate of the formulation of EP 256933. Therefore, the process described in EP 330532 led to a new dosage form in which the active ingredient, co-micronized with a solid surfactant, was able to show improved dissolution, and thus increased bioavailability, which makes it possible, for a given level of effectiveness, to decrease the daily dose of the medicament.

U.S. Pat. No. 4,895,726 teaches to improve fenofibrate bioavailability using a composition containing a comicronized mixture of particles of fenofibrate and a solid surfactant. The co-micronization was carried out in an accelerated air-jet mill until the powder obtained has a mean particle size is less than 15 microns. The powder was mixed with lactose and starch and granulated. The dried granules were mixed with polyvinylpyrrolidone and magnesium stearate and filled in gelatin capsules. U.S. Pat. No. 4,895,726 teaches that there is no statistically significant difference between the in vivo bioavailability of 200 mg of co-micronized fenofibrate according to the invention of U.S. Pat. No. 4,895,726 and 300 mg of non-micronized fenofibrate. In other words, this patent proved that co-micronized fenofibrate at a 200 mg dose is bioequivalent to a 300 mg dose of a non-micronized fenofibrate formulation according to EP 330532.

U.S. Pat. No. 4,800,079 describes a granular medicine based on fenofibrate, each granule comprising an inert core, a layer based on fenofibrate, and a protective layer. The medicine is characterized in that the fenofibrate is present in the form of crystalline microparticles having a size of less than 30 microns, and preferably less than 10 microns. The layer based on fenofibrate includes a binder selected from the group consisting of methacrylic polymers, polyvinylpyrrolidone, cellulose derivatives, and polyethylene glycols.

U.S. Pat. No. 7,101,574 describes a pharmaceutical composition in the form of granules, containing neutral microgranules, supporting a layer of a composition comprising micronized fenofibrate, a surfactant and, a cellulose binding cellulose derivative, preferably hydroxypropylmethylcellulose (HPMC), as a solubilizing adjuvant. The cellulose derivative represents less than 20 wt. % of the composition, while the fenofibrate is present in an amount greater than or equal to 60% by weight of the pharmaceutical composition. The pharmaceutical composition reported in U.S. Pat. No. 7,101,574 describes the fenofibrate:HPMC mass ratio as being between 5:1 and 15:1. The formulation disclosed in U.S. Pat. No. 7,101,574 provides enhanced bioavailability of the active principle. U.S. Pat. No. 7,101,574 compares the in vivo release profile of gelatin capsules containing the disclosed granules to gelatin capsules containing an equivalent dose of the formulation of EP 330532, marketed under the trade name Lipanthyl 200M. The maximum plasma concentration (Cmax) of the disclosed formulation under fasting conditions was reported to be 4.71 microgram/mL, compared to a Cmax of 2.35 microgram/mL attained with the formulation of EP 330532.

This present disclosure provides a formulation having a higher bioavailability than commercially available products containing fenofibrate, including ANTARA® Capsules, sold by Lupin Laboratories and containing 130 mg of fenofibrate. The ANTARA® Capsules are made according to the teachings of U.S. Pat. No. 7,101,574 and/or U.S. Pat. No. 7,863,331.

In various embodiments, the formulation of the present disclosure comprises Fenofibrate or a related drug, HPMC, a surfactant, such as sodium lauryl sulfate, an inert support, such as sugar spheres (20-45 mesh or 850-355 microns) and other excipients. In various embodiments, the inert supports may have a size of 35-45 mesh or 500-355 microns). In other embodiments, the inert supports may have a size of 20-25 mesh or 850-710 microns). The fenofibrate to HPMC weight ratio is between about 3.5:1 and about 4.5:1, and the amount of sodium lauryl sulfate is between about 0.3% and about 10% by weight. The fenofibrate formulation and method of manufacturing disclosed herein provides an improvement in Cmax, compared to ANTARA® capsules. In various embodiments, the fenofibrate formulation and method of manufacturing disclosed herein provides an improvement in Cmax without significantly affecting values for AUCL and/or AUCI, when compared to ANTARA® capsules. Various embodiments disclosed herein may afford an improvement in Cmax and an increase in AUCL and/or AUCI, compared to ANTARA® capsules.

SUMMARY

A summary of various embodiments is presented herein. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections. Various embodiments disclosed herein relate to a dosage form comprising an effective amount of fenofibric acid, pharmaceutically acceptable salts thereof, pharmaceutically acceptable esters thereof, or prodrugs thereof. In various embodiments, the active agent is fenofibrate, an ester of fenofibric acid which is hydrolyzed to fenofibric acid in vivo. Fenofibrate is a prodrug of fenofibric acid.

Various embodiments disclosed herein relate to a fenofibrate formulation comprising a dosage form containing a plurality of beads or particles. The beads or particles collectively comprise a pharmaceutical composition containing a drug selected from the group consisting of fenofibric acid, pharmaceutically acceptable salts thereof, pharmaceutically acceptable esters thereof, and prodrugs thereof; from 0.3% to 10% by weight of the beads or particles of a surfactant; and from about 5% to about 15% by weight of the beads or particles of a water soluble or water dispersible cellulosic binder. The beads or particles may comprise from about 20% to about 60% by weight of the drug. In various embodiments, the beads or particles may each comprise an inert core, with the pharmaceutical composition being coated on the inert core.

In various embodiments, the mass ratio of the drug to the binder in the dosage form is between about 3.5:1 and 4.5:1, preferably between about 3.8:1 and about 4.4:1, more preferably between about 3.9:1 and about 4.35:1. In some embodiments, the dosage form produces a first Cmax in vivo that is between about 10% and about 50% higher, preferably 20% to 45% higher, than a comparative Cmax produced by a comparative dosage form comprising the drug and the binder in a ratio of between 5:1 and 15:1, where the comparative dosage form further comprises 1% to 10% by weight of the surfactant. The dosage form disclosed herein and the comparative dosage form each contain equivalent amounts of the drug. Suitable examples of comparative dosage forms include the dosage forms described in the Examples of U.S. Pat. No. 7,863,331 and the Examples of U.S. Pat. No. 7,101,574.

In certain embodiments, where the pharmaceutical composition comprises about 45% to about 55% by weight of said drug, based on the weight of the beads or particles, the dosage form produces a Cmax in vivo that is between about 10% and about 30% higher than a comparative Cmax from the comparative dosage form. In other embodiments, where the pharmaceutical composition comprises about 25% to about 35% by weight of the drug, based on the weight of the beads or particles, the dosage form produces a Cmax in vivo that is between about 35% and about 50% higher than a comparative Cmax from the comparative dosage form.

In various embodiments, the dosage form comprises a plurality of first beads or first particles; and a plurality of second beads or second particles. Each of the first beads or first particles comprises from about 45% to about 55% by weight of the fenofibrate drug, from 0.3% to 10% by weight of a surfactant; and from about 5% to about 15% by weight of a water soluble or water dispersible cellulosic binder. The mass ratio of the drug to the binder in said first beads or first particles is between about 3.5:1 and 4.5:1. Each of the second beads or second particles comprises from about 25% to about 35% by weight of the fenofibrate drug, from 0.3% to 10% by weight of a surfactant; and from about 5% to about 15% by weight of a water soluble or water dispersible cellulosic binder. The mass ratio of the drug to the binder in the second beads or second particles is between about 3.5:1 and about 4.5:1. In various embodiments, the dosage form comprising a combination of first beads or first particles and second beads or second particles produces a Cmax in vivo that is greater than a Cmax produced by a dosage form containing only the first beads, and less than a Cmax produced by a dosage form containing only the second beads.

The dosage form comprising a combination of first beads or first particles and second beads or second particles contains from 20% to 80% by weight of the first beads or first particles, preferably between 30% and 70% by weight of the first beads or first particles, more preferably between 40% and 60% by weight of the first beads or first particles, based on the total weight of all beads or particles. The precise ratio of the first beads or first particles to the second beads or second particles may be adjusted to control Cmax. For example, a dosage form comprising 30% by weight of the first beads and 70% of the second beads will exhibit a higher Cmax than a dosage form comprising 70% by weight of the first beads and 30% of the second beads.

Various embodiments disclosed herein relate to a dosage form comprising a plurality of beads or particles, where the beads or particles comprise a pharmaceutical composition containing from about 20% to about 55% by weight of a drug selected from the group consisting of fenofibric acid, pharmaceutically acceptable salts thereof, pharmaceutically acceptable esters thereof, and prodrugs thereof; from 0.3% to 10% by weight of said beads or particles of a surfactant; and from about 5% to about 15% by weight of a water soluble or water dispersible cellulosic binder. The mass ratio of the drug to the binder in the dosage form is between about 3.5:1 and 4.5:1.

According to various embodiments described herein, the surfactant used in the pharmaceutical compositions disclosed herein may be anionic surfactants, nonionic surfactants, or cationic surfactants, preferably anionic surfactants. A preferred surfactant is sodium lauryl sulfate.

The standards for bioavailability depend on several natural log transformed parameters associated with the rate and extent of absorption. Specifically, bioavailability depends on the parameters Cmax, AUCL, and AUCI. the 90% confidence interval of the relative mean Cmax, AUCL, and AUCI of the test product to reference product should be within 80% to 125%.

Various embodiments disclosed herein relate to a dosage form which is more bioavailable than ANTARA® capsules having an equivalent amount of fenofibrate, and therefore is not bioequivalent to ANTARA® capsules having an equivalent amount of fenofibrate. Specifically, the dosage forms disclosed herein exhibit a higher Cmax than ANTARA® capsules having an equivalent amount of fenofibrate. The disclosed dosage form comprises a defined amount of fenofibrate, which may be between 40 and 200 mg fenofibrate, preferably between 40 and 160 mg micronized fenofibrate. In various embodiments, the disclosed composition has a high bioavailability, with a Cmax which is between 10% and 50% higher, preferably between 20% and 45% higher, than ANTARA® capsules having an equivalent amount of fenofibrate. In various embodiments, ratio of AUCL or AUCI of the disclosed composition to ANTARA® capsules having an equivalent amount of fenofibrate, falls with the range of 80% to 125%.

In various embodiments disclosed herein, the disclosed compositions have an AUCL or an AUCI value which is greater than the corresponding AUCL or AUCI value for ANTARA® capsules having an equivalent amount of fenofibrate, as well as a Cmax which is higher than the corresponding Cmax for ANTARA® capsules. More specifically, the disclosed compositions may have an AUCL or an AUCI value which is at least 10% greater, preferably 10% to 50% greater, more preferably 10% to 30% greater, than the corresponding AUCL or AUCI value for ANTARA® capsules.

Various dosage forms disclosed herein also have a higher bioavailability than the dosage forms described in the Examples of U.S. Pat. No. 7,863,331 and the Examples of U.S. Pat. No. 7,101,574.

Fenofibrate dosage forms disclosed herein may be used to reduce cholesterol levels in patients at risk of cardiovascular disease. The fenofibrate dosage forms disclosed herein reduce both low-density lipoprotein (LDL) and very low density lipoprotein (VLDL) levels, as well as increasing high-density lipoprotein (HDL) levels and reducing triglycerides level. The fenofibrate dosage forms disclosed herein may be used alone, or in conjunction with statins in the treatment of hypercholesterolemia and hypertriglyceridemia.

BRIEF DESCRIPTION OF THE DRAWINGS

In order to better understand various exemplary embodiments, reference is made to the accompanying drawings, wherein.

DETAILED DESCRIPTION

Figure 1:
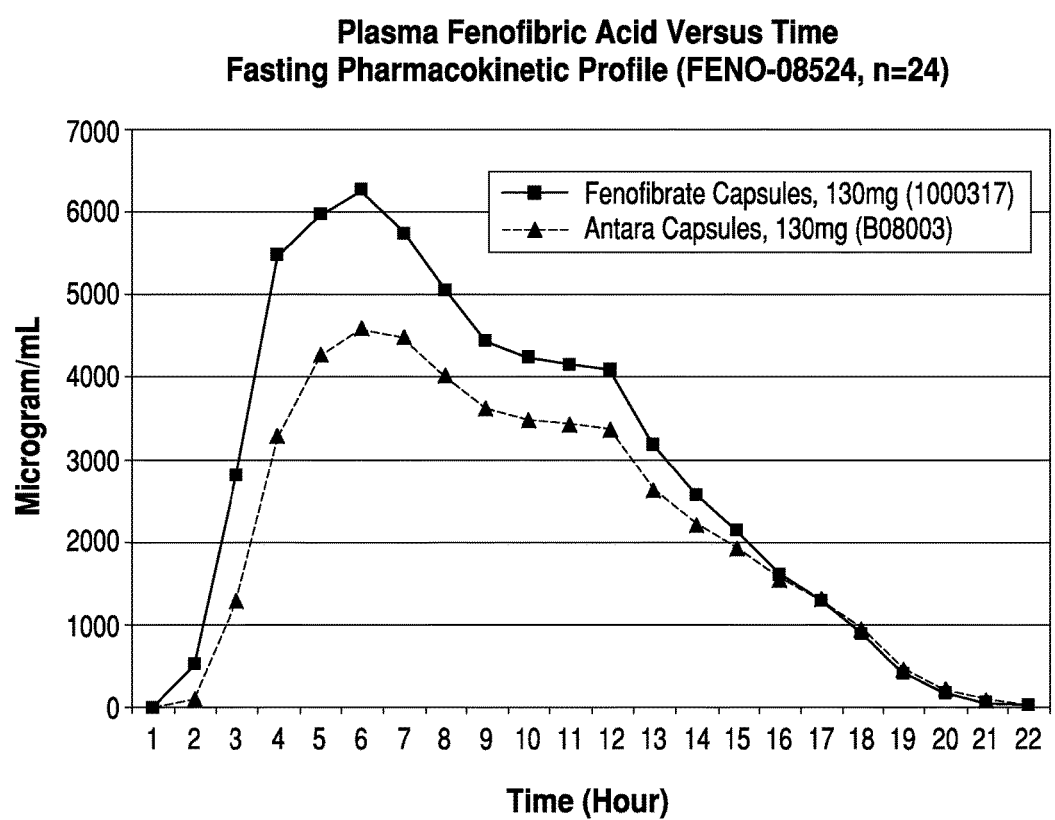
FIG. 1 shows the concentration of fenofibrate in plasma over time upon administration of 130 mg ANTARA® capsules and administration of 130 mg capsules according to Example 4.

1. Dosage Forms which are Bioequivalent to ANTARA® Capsules

Certain embodiments disclosed herein relate to dosage forms comprising a combination of high bioavailability beads and low bioavailability beads. In certain embodiments, the high bioavailability fenofibrate-containing beads contain micronized fenofibrate, a surfactant, and a binder which is water-soluble or water-dispersible. Suitable binders include hydroxypropylmethylcellulose (HPMC); hydroxypropyl cellulose; hydroxyethyl cellulose; carboxymethylcellulose; povidone and chitosan, with HPMC being a preferred binder. A suitable HPMC binder is commercially available under the trade name Pharmacoat® 603, from Harke Group.

In certain embodiments, the low bioavailability fenofibrate-containing beads contain micronized fenofibrate, and a binder which is water-soluble or water-dispersible. Suitable binders include hydroxypropylmethylcellulose (HPMC); hydroxypropyl cellulose; hydroxyethyl cellulose; carboxymethylcellulose; povidone and chitosan, with HPMC being a preferred binder.

In various embodiments, the high bioavailability fenofibrate-containing beads contain a surfactant in an amount of between about 0.3% by weight and about 10% by weight, preferably between about 0.5% by weight and about 5% by weight, more preferably between about 0.5% by weight and about 3% by weight. The low bioavailability fenofibrate-containing beads contain a surfactant in an amount of between about 0% by weight and about 0.25% by weight, preferably between about 0% by weight and about 0.05% by weight, more preferably 0% by weight.

The low bioavailability fenofibrate-containing beads (slow beads) and the high bioavailability fenofibrate-containing beads (fast beads) may be co-administered in a single dosage form. The low bioavailability fenofibrate-containing beads and the high bioavailability fenofibrate-containing beads may be combined and filled into a hard gelatin shell to form a capsule.

Alternatively, they may be combined with a water-soluble or water-dispersible binder, and compressed along with tableting excipients to form an immediate-release solid oral dosage form such as a tablet. Such compressed tablets may include a combination of slow beads and fast beads mixed together and combined with the binder and excipients prior to compression. As an alternative, slow beads may be mixed with the binder and excipients prior to a first compression step to form a first layer containing slow beads; and then the fast beads may be combined with the binder and excipients prior to a second compression step. In the second compression step, the formulation of fast beads and binder is deposited on the first layer, and the formulation of fast beads is compressed to form a bilayer tablet. If desired, suitable colorants may be added to either or both of the slow bead formulation and the fast bead formulation so that the layers of the bilayer tablet are visually distinguishable. Alternatively, the formulation of fast beads may be compressed initially to form the first layer, with the second layer containing the formulation of slow beads.

In various embodiments, the fast beads and the slow beads may be combined, and then blended with suitable excipients, including a binder, a water-soluble or water-dispersible filler, a disintegrant and/or a lubricant. The resulting mixture may be compressed into multiple mini-tablets, which may then be then encapsulated in a suitable size two piece hard gelatin capsule shell.

In other embodiments, the fast beads may be blended with suitable excipients, and then compressed into multiple mini-tablets. Similarly, the slow beads may be blended with suitable excipients, and then compressed into multiple mini-tablets. Mini-tablets containing the fast beads may be mixed with mini-tablets containing the slow beads, and the resulting admixture may then be then encapsulated in a suitable size two piece hard gelatin capsule shell. In various embodiments, the mini-tablets containing the fast beads and the mini-tablets containing the slow beads contain equal amounts of fenofibrate, and are combined in a predetermined ratio. In various embodiments, a capsule containing mini-tablets containing fast beads and mini-tablets containing slow beads contains from 50% to 80% of mini-tablets containing fast beads and from 20% to 50% of mini-tablets containing the slow beads.

In various embodiments, the dosage of fenofibrate may take the form of multiple tablets to be co-administered. In various embodiments, a first tablet may contain fenofibrate in the form of fast beads only (a fast tablet), while a second tablet may contain fenofibrate in the form of slow beads only (a slow tablet). With this approach, one slow tablet may be co-administered with at least one fast tablet, preferably from one to three fast tablets.

In various embodiments, one tablet containing fast beads or a combination of slow and fast beads may be prepared as disclosed herein, and then combined with a granulated powder of fenofibrate and encapsulated in a suitable size two piece hard gelatin capsule shell. Alternatively, a combination of fast beads and granulated powder of fenofibrate can be encapsulated to achieve the desired drug release profile.

In various embodiments, the slow and fast beads can also be manufactured by extrusion spheronization technology. As an alternative to slow and fast beads, the dosage forms disclosed herein may be manufactured from granules manufactured by spray drying techniques. For example, a slurry of fenofibrate, a cellulosic binder, and a surfactant in an amount of between about 0.3% by weight and about 10% by weight, based on solids content, may be spray dried to form fast granules. A slurry of fenofibrate, a cellulosic binder, and a surfactant in an amount of between about 0% by weight and about 0.25% by weight, based on solids content, may be spray dried to form slow granules. The fast and slow granules may be used as substitutes for fast and slow beads.

In various embodiments, the fenofibrate beads or granules can be used for manufacturing combination pharmaceutical products. In some embodiments, the combination products may contain fenofibrate and a second drug, such as a statin, niacin, or metformin. The combination products may be manufactured by applying a fenofibrate suspension onto a core material, where the core material contains at least one pharmaceutical active, such as a statin, niacin, or metformin.

In some embodiments, the slow and fast beads may be combined and filled into a unit dose sealed pouch. The contents of the pouch may be dispersed in a liquid such as juice or water, and the patient may drink the resulting dispersion.

In various embodiments, the ratio of the fast and slow beads (fast beads:slow beads) in the dosage forms disclosed herein is between 50:50 and 90:10, preferably between 60:40 and 90:10, most preferably between about 75:25 and 80:20. The beads disclosed herein may be prepared by spraying the drug layer suspension onto inert cores, preferably inert cores having a 20 to 50 mesh particle size, i.e., 300 microns to 850 microns. In some embodiments, the inert cores may have a mesh size of 20 to 25, i.e., from 710 to 850 microns. In other embodiments, the inert cores may have a mesh size of 35 to 45, i.e., from 355 to 500 microns. In further embodiments, the fast beads may be made from inert cores having a mesh size of between 20 mesh and 25 mesh, while the slow beads may be made from inert cores having a mesh size of between 35 mesh and 45 mesh. In other embodiments, the fast beads may be made from 35 to 45 mesh cores, while the slow beads may be made from 20 to 25 mesh cores.

In one embodiment, an HPMC binder is solubilized in water or a polar organic solvent. Micronized fenofibrate is added to the binder solution to form a drug suspension. The surfactant is added to the drug suspension. Optionally, an antifoaming agent is incorporated into the drug suspension. Suitable antifoaming agents include silicones, such as dimethicone. Suitable solvents include Class 3 solvents, i.e., solvents of low toxic potential. Preferred Class 3 solvents include polar solvents suitable for dissolving or dispersing HPMC, such as water, Acetone, Anisole, 1-Butanol, 2-Butanol, 3-Methyl-1-butanol, Methyl ethyl ketone, Methyl isobutyl ketone, 2-Methyl-1-propanol, Dimethyl sulfoxide, Ethanol, 1-Pentanol, 1-Propanol, and 2-Propanol, and mixtures thereof. The resulting drug suspension is homogenized, and then sprayed onto the sugar spheres. In various embodiments, the drug suspension is homogenized for a minimum of 8 hours, preferably 8 to 48 hours, more preferably 8 to 24 hours, most preferably 8 to 10 hours, prior to spraying onto the inert cores.

In various embodiments, the beads disclosed herein may be prepared by spraying the drug layer suspension onto inert cores made from insoluble inert materials, such as silicon dioxide, calcium phosphate dihydrate, dicalcium phosphate, calcium sulfate dihydrate, microcrystalline cellulose, cellulose derivatives, calcium carbonate, dibasic calcium phosphate anhydrous, dibasic calcium phosphate monohydrate, tribasic calcium phosphate, magnesium carbonate, magnesium oxide and activated carbon. In various embodiments, the beads disclosed herein may be prepared by spraying the drug layer suspension onto soluble cores, such as sugar spheres, more particularly, spheres of sugars selected from the group consisting of like dextrose, lactose, anhydrous lactose, spray-dried lactose, lactose monohydrate, mannitol, starches, sorbitol, and sucrose. Other materials which may be used as inert cores include insoluble inert plastic materials, such as spherical or nearly spherical core beads of polyvinylchloride or polystyrene. Mixtures of these core materials may be used. In certain embodiments, low bioavailability fenofibrate-containing beads (slow beads) may be prepared using a different core material from high bioavailability fenofibrate-containing beads (fast beads).

In various embodiments, the drug suspension is sprayed onto the inert cores contains a surfactant. Suitable surfactants include anionic surfactants, nonionic surfactants, cationic surfactants, or mixtures thereof. Preferably, the surfactants are anionic surfactants. Suitable anionic surfactants include sodium oleate, sodium dodecyl sulfate, sodium diethylhexyl sulfosuccinate, sodium dimethylhexyl sulfosuccinate, sodium di-2-ethylacetate, sodium 2-ethylhexyl sulfate, sodium lauryl sulfate; sodium undecane-3-sulfate, sodium ethylphenylundecanoate, and carboxylate soaps. Preferred anionic surfactants include C8 to C24 sulfate monoester surfactants. More preferred anionic surfactants include sodium 2-ethylhexyl sulfate, sodium lauryl sulfate; and sodium undecane-3-sulfate. Suitable cationic surfactants include benzalkonium halide salts. Suitable nonionic surfactants include C8-C28 ethoxylated alcohols, mono-, di-, and trimesters of glycerol, and Polysorbate 80. In various embodiments, low bioavailability fenofibrate-containing beads (slow beads) may be prepared using a different surfactant from high bioavailability fenofibrate-containing beads (fast beads). In various embodiments, the slow beads include from 0% to about 0.25% by weight of a surfactant, preferably from 0% to about 0.05% by weight of a surfactant, more preferably 0% by weight of a surfactant. In various embodiments, the fast beads include from about 0.3% to about 10% by weight of a surfactant, preferably from 0.3% to about 5% by weight of a surfactant, more preferably from about 0.5% to about 2% by weight of a surfactant.

In various embodiments, the slow beads contain between about 30% and about 80% micronized fenofibrate, relative to the total weight of the slow beads. Preferably, the slow beads contain between about 40% and about 59% micronized fenofibrate, more preferably between about 45% and about 55% micronized fenofibrate. The beads may contain between about 30% and about 59% micronized fenofibrate, relative to the total weight of the slow beads. Preferably, the fast beads contain between about 40% and about 59% micronized fenofibrate, more preferably between about 45% and about 55% micronized fenofibrate.

The fast beads disclosed herein contain fenofibrate and a binder in a ratio of fenofibrate:binder of from about 1:1 to less than 5:1, preferably from about 2:1 to about 4.5:1, more preferably from about 3.5:1 to about 4.5:1. In various embodiments, the binder is HPMC. In various embodiments, the fast beads disclosed herein contain fenofibrate and HPMC in a ratio of fenofibrate:HPMC of about 4:1. In some embodiments, the fast beads additionally comprise from 0.3% to about 10% by weight of sodium lauryl sulfate, preferably from 0.5% to about 2% by weight of sodium lauryl sulfate.

The slow beads disclosed herein contain fenofibrate and a binder in a ratio of fenofibrate:binder of from greater than 5:1 to about 15:1, preferably from about 6:1 to about 12:1, more preferably from about 7:1 to about 9:1. In various embodiments, the binder is HPMC, and the slow beads contain fenofibrate and HPMC in a ratio of fenofibrate:HPMC of about 8:1. In some embodiments, the slow beads additionally comprise from 0% to about 0.25% by weight of sodium lauryl sulfate, and are preferably free of sodium lauryl sulfate.

Fenofibrate, which is a prodrug of fenofibric acid, may be used as a micronized fenofibrate powder. The fenofibrate powder may be fenofibrate Form I as disclosed in U.S. Patent Publication 2009/0149533; fenofibrate Form II as disclosed in U.S. Patent Publication 2009/0149533; amorphous fenofibrate; hydrates or solvates of fenofibrate, or a mixture thereof. Fenofibrate may be partially or completely replaced with fenofibric acid; pharmaceutically acceptable salts of fenofibric acid; C1 to C5 esters or prodrugs of fenofibric acid, or a mixture thereof.

In various embodiments, the fast and slow beads are made using micronized fenofibrate with a weight-average particle diameter (D50) of between 1 and 15 microns, preferably between 4 and 10 microns. Preferably, the fast and slow beads are made using micronized fenofibrate where at least 99% of the fenofibrate particles have a particle diameter of less than 50 microns.

2. Dosage Forms which are More Bioavailable than ANTARA® Capsules

Various embodiments disclosed herein provide fenofibrate dosage forms comprising a faster (higher bioavailability) formulation than commercially available products containing fenofibrate, including ANTARA® Capsules, sold by Lupin Laboratories and containing 130 mg of fenofibrate. Various embodiments of the formulation disclosed herein comprise fenofibric acid, a salt thereof, a derivative thereof, or a prodrug thereof. A suitable formulation includes fenofibrate, an ester prodrug of fenofibric acid which undergoes hydrolysis in vivo.

Various embodiments of the dosage form disclosed herein include beads or particles containing a drug, which may be fenofibric acid or a salt or ester thereof;

from 0.3% to 10% by weight of the beads or particles of a surfactant; and from about 5% to about 15% by weight of the beads or particles of a water soluble or water dispersible cellulosic binder. In various embodiments, the mass ratio of the drug to the binder in said dosage form is between about 3.5:1 and 4.5:1, preferably between about 3.8 and about 4.4, more preferably between about 3.9 and about 4.35.

In various embodiments, a formulation comprising fenofibric acid or a salt or ester thereof; from 0.3% to 10% by weight of a surfactant; and from about 5% to about 15% by weight of a water soluble or water dispersible cellulosic binder may be converted into particles or granules by conventional methods. Suitable methods include spray-drying a solution of fenofibrate, a surfactant, and a water soluble or water dispersible cellulosic binder to form solid granules. In certain embodiments, a solution of fenofibrate, a surfactant, and a water soluble or water dispersible cellulosic binder may be sprayed onto inert cores to form solid granules.

In various embodiments, the formulation comprises beads or granules made from fenofibrate, HPMC, sodium lauryl sulfate, and inert cores. The beads or granules disclosed herein may be prepared by spraying a drug layer suspension comprising a solvent, fenofibrate, HPMC, and sodium lauryl sulfate onto inert cores, preferably inert cores having a 20 to 50 mesh particle size, i.e., 300 microns to 850 microns. In some embodiments, the inert cores may have a mesh size of 20 to 25, i.e., from 710 to 850 microns. In other embodiments, the inert cores may have a mesh size of 35 to 45, i.e., from 355 to 500 microns. In further embodiments, the beads or granules may comprise a first population of beads from inert cores having a mesh size of between 20 mesh and 25 mesh, and a second population of beads from inert cores having a mesh size of between 35 mesh and 45 mesh.

In certain embodiments, an HPMC binder is solubilized in water or a polar organic solvent. Micronized fenofibrate is added to the binder solution to form a drug suspension. The surfactant is added to the drug suspension. Optionally, an antifoaming agent is incorporated into the drug suspension. Suitable antifoaming agents include silicones, such as dimethicone. Suitable solvents include polar solvents suitable for dissolving or dispersing HPMC, such as water, Acetone, Anisole, 1-Butanol, 2-Butanol, 3-Methyl-1-butanol, Methyl ethyl ketone, Methyl isobutyl ketone, 2-Methyl-1-propanol, Dimethyl sulfoxide, Ethanol, 1-Pentanol, 1-Propanol, and 2-Propanol, and mixtures thereof. The resulting drug suspension is homogenized, and then sprayed onto the sugar spheres. In various embodiments, the drug suspension is homogenized for a minimum of 8 hours, preferably 8 to 48 hours, more preferably 8 to 24 hours, most preferably 8 to 10 hours, prior to spraying onto the inert cores.

In various embodiments, the beads disclosed herein may be prepared by spraying the drug layer suspension onto inert cores made from insoluble inert materials, such as silicon dioxide, calcium phosphate dihydrate, dicalcium phosphate, calcium sulfate dihydrate, microcrystalline cellulose, cellulose derivatives, calcium carbonate, dibasic calcium phosphate anhydrous, dibasic calcium phosphate monohydrate, tribasic calcium phosphate, magnesium carbonate, magnesium oxide and activated carbon. In various embodiments, the beads disclosed herein may be prepared by spraying the drug layer suspension onto soluble cores, such as sugar spheres, more particularly, spheres of sugars selected from the group consisting of like dextrose, lactose, anhydrous lactose, spray-dried lactose, lactose monohydrate, mannitol, starches, sorbitol, and sucrose. Other materials which may be used as inert cores include insoluble inert plastic materials, such as spherical or nearly spherical core beads of polyvinylchloride or polystyrene. Mixtures of these core materials may be used.

In various embodiments, the inert cores may be sugar spheres (35-45 mesh or 355 to 500 microns). The fenofibrate to HPMC weight ratio is between 3.5:1 and 4.5:1, and the surfactant is used in an amount of between about 0.3 wt. % and about 10 wt. %. In various embodiments, the surfactant is an anionic surfactant, such as sodium lauryl sulfate (SLS). In various embodiments, the amount of sodium lauryl sulfate is 0.3% to 10% w/w, preferably 0.4% to 5% w/w, more preferably 0.5% to 2% w/w. The aqueous drug suspension containing fenofibrate, HPMC, sodium lauryl sulfate and simethicone was mixed for a minimum of 8 hours in a Ross Mixer before spraying on to the fluidized sugar sphere substrates in a ROTOR granulator. The fenofibrate formulation and method of manufacturing of this present invention provides an improvement in Cmax by 1.2 times than that of the commercial formulation (ANTARA®) and/or an AUC improvement of at least 1.4 times than that of the commercial formulation ANTARA® capsules when dosed in the fasted state.

In various embodiments, the formulation comprises Fenofibrate, HPMC, sodium lauryl sulfate, sugar spheres (35-45 mesh or 355-500 microns) and other excipients. The fenofibrate to HPMC weight ratio may be about 4±0.2 to about 1, and the amount of sodium lauryl sulfate may be about 0.5 to about 2% w/w. The fenofibrate formulation and method of manufacturing of this present invention provides a value of Cmax which is 10% to 50%, preferably 20% to 45%, higher than that of the commercial formulation (ANTARA®) and/or a value of AUC which is 10% to 60%, preferably 15% to 50%, more preferably 20 to 45%, higher than that of ANTARA® capsules when dosed in the fasted state. In this present invention, the absorption of fenofibrate in fasted healthy volunteers is significantly ($P<0.05$) enhanced when compared to the commercial formulation such as ANTARA® 130 mg capsules.

An embodiment of the invention is directed to a fenofibrate, composition wherein the pharmacokinetic profile of the composition resulted in higher bioavailability than ANTARA® Capsules, 130 mg, in particular as defined by Cmax and AUC guidelines given by the U.S. Food and Drug Administration. The increase in bioavailability may permit a reduction in total dosage for some patients. The improved bioavailability may allow administration of smaller doses of fenofibrate to achieve equivalent pharmacokinetics profiles.

3. EXAMPLES

Various embodiments will be described in the following non-limiting examples. In the following examples, sugar spheres were used as the base substrate onto which the drug suspension was sprayed. The drug suspension was sprayed onto the sugar spheres in a fluidized bed fitted with a ROTOR Insert. The sugar spheres had a 20-25 mesh particle size distribution, providing a uniform surface area for drug layering.

The micronized fenofibrate used in the following examples had a weight average particle size D50 of between 5 and 7 microns, with at least 99% of particles having a particle size of <50 microns (D99); at least 90% of particles having a particle size of <15 microns (D90); and no more than 10% of particles having a particle size of <1 micron (D10).

Purified water was selected as a solvent for preparation of the drug suspension, as it provides a suitable medium for dissolving the hypromellose binder and suspending the micronized fenofibrate drug substance.

Hypromellose (Pharmacoat® 603) was used as a binder in the drug suspension, as it aids in adhering the drug to the sugar sphere substrate during processing. Sodium lauryl sulfate (SLS) was used as a surfactant in preparing the fast beads. Sodium lauryl sulfate is a commonly used excipient in solid oral dosage forms to enhance wetting and improve drug dissolution rate. This excipient is employed to enhance the aqueous wettability of fenofibrate in the drug layering suspension and to enhance the drug release from the high bioavailability, or fast, drug layered beads. Sodium lauryl sulfate was not used in the slow beads in the following examples, resulting in reduced drug release from the slow beads.

Simethicone, an antifoaming agent, was incorporated in the drug suspension to minimize the potential to generate foam during preparation of the drug layering suspension.

In some examples, approximately 0.1% w/w micronized talc was blended with the Fenofibrate Intermediate Beads, Type B prior to encapsulation to dissipate static charge and ensure efficient filling during encapsulation.

In various examples discussed below, formulations disclosed herein were administered to healthy adult volunteers in bioequivalence studies under fasting and fed conditions. The bioavailability achieved with the formulations disclosed herein is comparable to the bioavailability achieved with the administration of Lupin's ANTARA® capsules, where the ANTARA® capsules contain a single population of granules having a defined concentration of fenofibrate. The formulations disclosed herein include two populations of fenofibrate beads, including fast beads which have a higher bioavailability than the beads in ANTARA® capsules, and slow beads which have a lower bioavailability than the beads in ANTARA® capsules.

Manufacturing Process: The manufacture of Fenofibrate Intermediate Beads or Pellets or Particles involves: Drug Suspension Manufacturing ⇒ Rotor Drug Layering ⇒ Fluid Bed Drying ⇒ Screening Via Mesh ⇒ Final Blending. The manufacturing process was shown to provide Fenofibrate Intermediate Beads with acceptable assay and content uniformity characteristics.

Manufacture of Fenofibrate Capsules (Micronized) proceeds via encapsulation of Fenofibrate Intermediate Beads. In certain embodiments disclosed herein, capsules are prepared from a homogeneous population of Fenofibrate Intermediate Beads. These beads may comprise fenofibrate; from 0.3% to 10% by weight of a surfactant; and from about 5% to about 15% by weight of a water soluble or water dispersible cellulosic binder, where the mass ratio of fenofibrate to the binder s between about 3.5:1 and 4.5:1. The homogeneous population of Fenofibrate Intermediate Beads is supplied to a capsule filing station, which is used to prepare dosage forms by encapsulating the population of beads in appropriately sized capsule shells, preferably gelatin capsule shells.

In some embodiments, dosage forms are prepared from a heterogeneous population of Fenofibrate Intermediate Beads. The heterogeneous population of Fenofibrate Intermediate Beads may be prepared by combining at least two types of fenofibrate beads having different release properties to form a blend. The blend may be prepared first, and then filled into capsule shells using a single capsule filling station. Alternatively, capsules may be prepared using two or more capsule filling stations. Filling station I may be used to fill a first type of Fenofibrate Intermediate Beads into a capsule shell, and Filling station II may then be used to encapsulate a second type of Fenofibrate Intermediate Beads into the capsule shell, where the first and second types of beads are different. The manufacturing process was shown to provide a finished product with acceptable assay and content uniformity characteristics.

Drug Layer Suspension Manufacturing: The drug layer suspension in this invention is manufactured using a high speed homogenizer mixer (Ross Model HSM 105, attached with a rotor/stator mixing blade used for the large scale manufacturing). During experimentation, several different types of mixer/disperser mixing head attachments were evaluated: slotted rotor/stator disperser, saw tooth disperser, slotted stator, and a fine screen stator with slotted disperser. Table 1 summarizes the formulation compositions and the drug release characteristics from these experiments. All formulations processed well and their drug release characteristics were similar, indicating that mixer type has no impact on formulation performance. Based on this evaluation, the rotor/stator configuration was chosen for the manufacture of the drug layering suspension. In addition, the process requires the suspension to be mixed with a homogenizer mixer for a minimum of 8 hours prior to drug layering, with continuous agitation of the suspension maintained throughout the drug layering process. The homogenization time minimum of 8 hours can be further reduced, based on processing efficiency.

TABLE 1

Fenofibrate Capsules USP, 130 mg
Evaluation of Homogenizer Mixing Head

| | Slotted Rotor/Stator | | Saw tooth | | Slotted Stator | | Fine screen stator w/dispersator | |
|---|---|---|---|---|---|---|---|---|
| | X07-047-58A4 | % | X07-047-58A5 | % | X07-047-58A6 | % | X07-047-58A7 | % |
| Part I | | | | | | | | |
| Sugar Spheres (#35-#45) | 279.5 | 62.1 | 279.5 | 62.1 | 279.5 | 62.1 | 279.5 | 62.1 |
| Part II | | | | | | | | |
| Fenofibrate (Micronized) | 130.0 | 28.9 | 130.0 | 28.9 | 130.0 | 28.9 | 130.0 | 28.9 |
| Sodium Lauryl Sulfate | 9.0 | 2.00 | 9.0 | 2.00 | 9.0 | 2.00 | 9.0 | 2.00 |
| Pharmacoat 603 (Hypromellose) | 31.5 | 7.0 | 31.5 | 7.0 | 31.5 | 7.0 | 31.5 | 7.0 |
| Purified Water* | (682.0) | | (682.0) | | (682.0) | | (682.0) | |
| Total | 450.0 | | 450.0 | | 450.0 | | 450.0 | |

TABLE 1-continued

Fenofibrate Capsules USP, 130 mg
Evaluation of Homogenizer Mixing Head

| ANTARA ® 130 mg | | Dissolution condition: 1000 mL purified water, 0.01M sodium lauryl sulfate, USP Apparatus 2, at 75 rpm | | | |
|---|---|---|---|---|---|
| Time | 0.01M SLS | 0.01M SLS | 0.01M SLS | 0.01M SLS | 0.01M SLS |
| 10 min | 21% | 19% | 21% | 21% | 19% |
| 15 min | 24% | 19% | 21% | 21% | 18% |
| 20 min | 24% | 19% | 21% | 21% | 18% |
| 30 min | 24% | 18% | 21% | 21% | 18% |
| 40 min | 24% | 18% | 21% | 21% | 18% |
| 60 min | 24% | 18% | 21% | 21% | 18% |

*Purified water removed during processing

Description of Rotor Drug Layering Process: The fluidization pattern in the rotor processor can be best characterized as a spiraling helix. Three factors act on the beads or pellets or particles (materials) to produce this flow pattern. The rotating disk of the ROTOR insert provides centrifugal force which forces the rotating materials toward the wall of the processing chamber at the periphery of the rotor insert, while conditioned upward airflow through the rotor gap develops a vertical force causing the materials to become fluidized. The fluidization air pushes the moving materials upward into the expansion chamber until gravity overcomes the upward air velocity and the material falls toward the center of the disk where there is little air movement. The drug layer suspension is sprayed tangentially onto the rotating particles, while heated process air causes the applied drug layer suspension to dry before the particles move again into the spraying zone. This cyclical process is repeated many hundreds of times until the appropriate quantity of solids are applied to the rotating core substrate (material).

The efficiency of the drug layering process is dependent on the relationship between particle movement within the processor, drug layering suspension spray rate and the rate of solvent evaporation. The movement of the particles during rotor drug layering process is dependent on rotor speed and air flow. Rotor speed is considered a critical parameter since it can affect the integrity of the beads. Slow speeds can lead to product agglomeration while excessive speeds can cause attrition. Rotor speed is adjusted to maintain proper particle movement as the weight of the batch increases during drug layering process. Once proper movement of the particle bed is established, the deposition of drug layering solids onto the core substrate is controlled by the rate at which drug layering suspension is applied to core beads or pellets, and the rate at which solvent is removed from the system. The example of appropriate process parameters (inlet air temperature, product temperature, air flow, spray rate, nozzle atomizing air pressure, nozzle size and Rotor speed) utilized for manufacturing the beads in large scale batches utilizing FL-Multi-60 with a Rotogranulator Insert are summarized in the following Table 2.

TABLE 2

Rotor drug layering Process Parameters for manufacturing the beads or pellets or particles using a 30" rotor inserted with a FL-Multi-60 Fluid Bed Dryer. Batch Size: 50 kg

| | Example 4 | | Example 6 | Example 7 | |
|---|---|---|---|---|---|
| | R&D-I1976 | R&D-I1975 | R&D-I 2052 | R&D-I2133 | R&D-I2128 |
| Inlet Temperature (° C.) | 50-65 | 54-65 | 53-64 | 52-67 | 56-69 |

TABLE 2-continued

Rotor drug layering Process Parameters for manufacturing the beads or pellets or particles using a 30" rotor inserted with a FL-Multi-60 Fluid Bed Dryer. Batch Size: 50 kg

| | Example 4 | | Example 6 | Example 7 | |
|---|---|---|---|---|---|
| | R&D-I1976 | R&D-I1975 | R&D-I 2052 | R&D-I2133 | R&D-I2128 |
| Product Temperature (° C.) | 31-34 | 30-35 | 30-32 | 34-32 | 36-36 |
| Air Flow (CFM) | 509-672 | 507-671 | 503-660 | 503-674 | 499-652 |
| Rotor Speed (rpm) | 100-125 | 100-125 | 100-125 | 99-125 | 100-125 |
| Rotor Gap | 4.0-6.0 | 4.0-6.0 | 4.0-6.0 | 4.0-6.5 | 4.0-6.0 |
| Atomization Air Pressure (psi) | 55 | 55 | 55 | 55 | 55 |
| Spray Rate (g/min) | 107-267 | 100-267 | 100-267 | 87-287 | 93-273 |
| Spray Nozzle Tip Size (mm) | 1.2 | 1.2 | 1.2 | 1.2 | 1.2 |

Example 1

Two formulations of fenofibrate containing beads were prepared. Each formulation was prepared by spraying a fenofibrate suspension onto sugar spheres having a size of 35 to 45 mesh in a fluidized bed. In one formulation (designated X07-047-58A1), the drug suspension included fenofibrate and HPMC in a ratio of 4:1, while in the other formulation (designated X07-047-62A1), the drug suspension included fenofibrate and HPMC in a ratio of 2.4:1 were evaluated. The amounts of the various ingredients are set forth in Table 3 below. The bead formulations are prepared in a fluidized bed by spraying a water-based suspension of micronized fenofibrate, HPMC, and sodium lauryl sulfate onto the sugar spheres.

TABLE 3

Fenofibrate Capsules USP, 130 mg
(Compositions containing 7% w/w or 12% w/w Pharmacoat 603 as a binder)

| | X07-047-58A1 (7% Pharmacoat 603) | | X07-047-62A1 (12% Pharmacoat 603) | |
|---|---|---|---|---|
| | mg | % | mg | % |
| Part I | | | | |
| Sugar Spheres (35-45 mesh) | 279.5 | 62.1 | 257.0 | 57.1 |
| Part II | | | | |
| Fenofibrate Jet Milled (Micronized) | 130.0 | 28.9 | 130.0 | 28.9 |

TABLE 3-continued

Fenofibrate Capsules USP, 130 mg
(Compositions containing 7% w/w or
12% w/w Pharmacoat 603 as a binder)

|  | X07-047-58A1 (7% Pharmacoat 603) | | X07-047-62A1 (12% Pharmacoat 603) | |
|---|---|---|---|---|
|  | mg | % | mg | % |
| Sodium Lauryl Sulfate | 9.0 | 2.0 | 9.0 | 2.0 |
| Pharmacoat 603 (HPMC, Hypromellose) | 31.5 | 7.0 | 54.0 | 12.0 |
| Purified Water* | (682.0) |  | (956.0) |  |
| Total | 450.0 |  | 450.0 |  |

*Removed during processing and does not contribute to the dry weight.

TABLE 4

Dissolution of Fenofibrate Capsules USP
Dissolution condition: 1000 mL purified water, 0.01M
Sodium Lauryl Sulfate (SLS), USP Apparatus 2, at 75 rpm

| Time | ANTARA® 0.01M SLS | X07-047-58A1 0.01M SLS | X07-047-62A1 0.01M SLS |
|---|---|---|---|
| 10 min | 21% | 21% | 20% |
| 15 min | 24% | 21% | 20% |
| 20 min | 24% | 21% | 20% |
| 30 min | 24% | 21% | 19% |
| 40 min | 24% | 21% | 19% |
| 60 min | 24% | 21% | 19% |

The formulation with 7% HPMC and the branded product ANTARA® yielded similar drug release characteristics in 1000 mL purified water containing 0.01 M sodium lauryl sulfate, USP Apparatus 2, at 75 rpm, as seen in Table 4.

Example 2

The effect of a nonionic surfactant or wetting agent on the formulation was studied by evaluating the in vitro drug release characteristics of capsules containing beads. In these formulations, the drug to binder (Fenofibrate:HPMC) ratio was kept constant at 4:1, as seen in Table 5 below. The X07-047-64A1 was formulated without any surfactant, whereas the X07-047-65A1 was formulated with 2% Polysorbate 80. These formulations were manufactured by mixing micronized fenofibrate, HPMC, and Polysorbate 80 in water to form a drug suspension, and spraying the drug layer suspension onto the 35-45 mesh sugar spheres in a fluidized bed dryer inserted with a ROTOR.

TABLE 5

Fenofibrate Capsules USP, 130 mg - Compositions
Effect of a non-ionic surfactant, Polysorbate 80

|  | X07-047-64A1 7% Pharmacoat, No Surfactant | | X07-047-65A1 7% Pharmacoat, 2% Polysorbate 80 | |
|---|---|---|---|---|
|  | mg | % | mg | % |
| Part I |  |  |  |  |
| Sugar Spheres (35-45 mesh) | 288.5 | 64.1 | 279.5 | 62.1 |
| Part II |  |  |  |  |
| Fenofibrate Jet Milled (Micronized) | 130.0 | 28.9 | 130.0 | 28.9 |

TABLE 5-continued

Fenofibrate Capsules USP, 130 mg - Compositions
Effect of a non-ionic surfactant, Polysorbate 80

|  | X07-047-64A1 7% Pharmacoat, No Surfactant | | X07-047-65A1 7% Pharmacoat, 2% Polysorbate 80 | |
|---|---|---|---|---|
|  | mg | % | mg | % |
| Polysorbate 80 | 0.0 | 0.0 | 9.0 | 2.0 |
| Pharmacoat 603 (Hypromellose) | 31.5 | 7.0 | 31.5 | 7.0 |
| Purified Water | (682.0) |  | (682.0) |  |
| Total | 450.0 |  | 450.0 |  |

TABLE 6

Dissolution of Fenofibrate Capsules USP
Dissolution condition: 1000 mL purified water, 0.01M
sodium lauryl sulfate, USP Apparatus 2, at 75 rpm

| Time | ANTARA 0.01M SLS | X07-047-64A1 0.01M SLS | X07-047-65A1 0.01M SLS |
|---|---|---|---|
| 10 min | 21% | 21% | 20% |
| 15 min | 24% | 21% | 20% |
| 20 min | 24% | 21% | 20% |
| 30 min | 24% | 20% | 20% |
| 40 min | 24% | 20% | 20% |
| 60 min | 24% | 20% | 20% |

The formulations with 7% HPMC yielded similar drug release characteristics in 1000 mL purified water containing 0.01 M sodium lauryl sulfate, USP Apparatus 2, at 75 rpm, to the drug release characteristics of the branded product ANTARA®, as seen in Table 6. This result was seen regardless of the presence or absence of a nonionic surfactant.

Example 3

Fenofibrate Dosage Forms which are More Bioavailable than ANTARA® Capsules

A formulation containing fenofibrate and HPMC in a ratio of 4:1 was evaluated. The formulation additionally contained 2%, by weight of the formulation, of the anionic surfactant SLS, as seen in Table 7. A drug suspension containing micronized fenofibrate, HPMC (hypromellose, Pharmacoat 603), sodium lauryl sulfate, and the antifoaming agent simethicone, a mixture of polydimethylsiloxane and hydrated silica gel, was prepared in purified water, and sprayed onto 35-45 mesh sugar spheres in a large scale fluid bed dryer (FL-M-60) equipped with a rotor granulator insert to produce the drug layered intermediate beads. Simethicone was incorporated to the drug layering suspension at a low level (0.044% w/w) to minimize foaming during preparation. Following drug layering, the dried beads were blended with micronized talc, screened to remove agglomerates, and machine encapsulated into the two piece hard gelatin capsules (size#0EL). Table 7 presents a summary of the composition.

TABLE 7

Fenofibrate Capsules USP, 130 mg (Lot 1000317) Composition
(Contains Fenofibrate Beads: 2% SLS, 4:1 Drug:HPMC)

|  | mg/g | % |
|---|---|---|
| Part I (Drug Layer Suspension) | | |
| Fenofibrate Micronized Intermediate | 130.0 | 28.87 |
| Hypromellose 2910 (Pharmacoat 603) | 31.5 | 7.0 |
| Sodium Lauryl Sulfate (Empicol LX/N) | 9.0 | 2.0 |
| Simethicone | 0.198 | 0.044 |
| Purified Water, USP | (342.0) | |

TABLE 7-continued

Fenofibrate Capsules USP, 130 mg (Lot 1000317) Composition
(Contains Fenofibrate Beads: 2% SLS, 4:1 Drug:HPMC)

|  | mg/g | % |
|---|---|---|
| Part II | | |
| Sugar Spheres (35/45 mesh) | 279.297 | 62.035 |
| Total | 450.0 | |
| Talc, Micronized | 0.225 | 0.05 |
| Total | 450.22 | |

The in vitro drug release of the above formulation was evaluated in a 1000 mL purified water containing 0.05 M SLS using USP Apparatus II at 75 rpm. Table 8 below summarizes the dissolution characteristics.

TABLE 8

Fenofibrate Capsules USP, 130 mg (Lot 1000317)
Dissolution Condition: USP Apparatus II, 75 rpm, 1000 mL, 0.05M SLS

| Product | 10 min | 15 min | 20 min | 30 min | 40 min | 60 min |
|---|---|---|---|---|---|---|
| ANTARA Capsules, 130 mg; B080033 | 54% | 74% | 84% | 93% | 97% | 100% |
| Fenofibrate Capsules, 130 mg #1000317 | 54% | 69% | 78% | 92% | 99% | 101% |

As seen in Table 8 above, the drug release rate of the formulation set forth in Table 7 (2% SLS, 4:1 Drug:HPMC) is comparable to the drug release rate of the branded product ANTARA®. Both formulations release 54% of the incorporated fenofibrate in 10 minutes; 92% to 93% of the incorporated fenofibrate in 30 minutes; and substantially all of the incorporated fenofibrate in 60 minutes.

The formulation of Table 7 was assessed in a pilot bioequivalence study, and compared to ANTARA® Capsules. Both the formulation of Table 7 and the ANTARA® Capsules contained 130 mg fenofibrate. The pilot bioequivalence study was an open-label, single-dose, randomized, two-period, two-treatment crossover study, using 24 normal healthy subjects. A summary of the pharmacokinetic data is presented in Table 9. FIG. 1 presents the pharmacokinetic profile of the formulations in Table 7.

TABLE 9

Fenofibrate Capsules USP, 130 mg (Lot 1000317)
Initial Pilot Bioequivalence Study Results - Fasting (n = 24) Conditions, Study (FENO-08254)

| | Fenofibric Acid - AUCL | | | | Fenofibric Acid - CPEAK | | | | |
|---|---|---|---|---|---|---|---|---|---|
| Lot # | Mean (ng · hr/mL) | Ratio (M/I) | 90% CI | Intra subject % CV | Mean ng/mL | Ratio (M/I) | 90% CI | Intra subject % CV | Tpeak (hours) |
| 1000317 | 141825 | 1.10 | 104.6-115.5 | 10 | 6549.0 | 1.41 | 128.1-154.9 | 19.3 | 3.45 |
| B08003-ANTARA | 127830 | | | | 4750.0 | | | | 4.13 |

The FDA has provided guidance for bioequivalence between a branded product and a generic equivalent. In general, bioequivalence depends on several natural log transformed parameters associated with the rate and extent of absorption. Specifically, the entire 90% confidence interval for the ratio of the test to reference area under the curve from zero to the last detectable concentration, AUCL, must fall between 80 and 125% of the corresponding AUCL of the branded product for therapeutic equivalence. Additionally, the entire 90% confidence interval for the ratio of the test to reference maximum plasma concentration, Cmax, must also fall between 80 and 125% of the corresponding Cmax of the branded product for therapeutic equivalence to be declared.

The results of Table 9 indicate that the formulation of Table 7 exhibited a similar extent of absorption (AUCL) compared to ANTARA® capsules, but showed elevated drug concentration in the plasma. The 90% confidence interval for the AUCL is 104.6-115.5%, which falls within the FDA's desired confidence interval ratio of 80%-125%. However, the Cmax parameter for the formulation of Table 7 is 138% of the corresponding value for the branded product, with a 90% confidence interval of 128.1%-155%. This result falls outside the FDA's desired confidence interval ratio of 80%-125%. Accordingly, the formulation of Table 7 exhibits higher bioavailability under fasting conditions than the reference product ANTARA®. The beads prepared in this formulation may be combined with slow beads, and used as fast beads in a formulation which is bioequivalent to ANTARA® capsules. Alternatively, the beads prepared in this formulation may be used as the only beads in a formulation which has a greater bioavailability than ANTARA® capsules. As seen in the results of Table 9, a 130 mg fenofibrate capsule containing only beads prepared according to Example 3 would show a moderate increase in AUCL of about 10%, when compared to the branded product ANTARA®. Further, a 130 mg fenofibrate capsule containing only beads prepared according to Example 3 would show a pronounced increase in Cmax of about 40%, when compared to the branded product ANTARA®.

Example 4

Fenofibrate Dosage Forms which are More Bioavailable than ANTARA® Capsules

Two different formulations containing 0.5% w/w sodium lauryl sulfate as a surfactant or 2% w/w sodium lauryl sulfate were manufactured. Both formulations contained fenofibrate and HPMC in a 4:1 ratio, as seen in Table 10. A drug suspension containing micronized fenofibrate, with a mean particle size of 10 microns, HPMC (hypromellose, Pharmacoat 603), sodium lauryl sulfate, and the antifoaming agent simethicone, a mixture of polydimethylsiloxane and hydrated silica gel, was prepared in purified water, and sprayed onto 20-25 mesh sugar spheres in a large scale fluid bed dryer (FL-M-60) equipped with a rotor granulator insert to produce the drug layered intermediate beads. A ratio of 4:1 fenofibrate to HPMC was used in the following formulations. Following the drug layering, the dried beads were blended with micronized talc, screened to remove the agglomerates and machine encapsulated using two piece hard gelatin capsules (size#0EL).

TABLE 10

Fenofibrate Capsules USP, 130 mg, #1000374
Fenofibrate Beads (520.0 mg/gram), Lot#R&D-I1976, 2% SLS, 4:1 Drug:Pharmacoat 603
Fenofibrate Capsules USP, 130 mg, #1000375
Fenofibrate Beads (520.0 mg/gram), Lot#R&D-I1975, 0.5% SLS, 4:1 Drug:Pharmacoat 603

| | Fenofibrate Capsules, 130 mg #1000374 | | | | Fenofibrate Capsules, 130 mg #1000375 | | | |
|---|---|---|---|---|---|---|---|---|
| | Fenofibrate Intermediate R&D-I1976, 2% SLS, 4:1 Drug:HPMC | | Fenofibrate Capsules, 130 mg, #1000374 | | Fenofibrate Intermediate R&D-I1975, 0.5% SLS, 4:1 Drug:HPMC | | Fenofibrate Capsules, 130 mg, #1000375 | |
| | mg/g | % | mg/capsule | % | mg/g | % | mg/capsule | % |
| Part I-Drug Layer Suspension | | | | | | | | |
| Fenofibrate Micronized | 520.0 | 52.0 | 130.0 | 51.95 | 520.0 | 52.0 | 130.0 | 51.95 |
| Pharmacoat 603 (Hypromellose) | 126.0 | 12.6 | 31.5 | 12.6 | 126.0 | 12.6 | 31.5 | 12.6 |
| Sodium Lauryl Sulfate | 20.0 | 2.0 | 5.0 | 2.0 | 5.0 | 0.5 | 1.25 | 0.5 |
| Simethicone | 0.22 | 0.022 | 0.055 | 0.022 | 0.22 | 0.022 | 0.055 | 0.022 |
| Purified Water* | (2735.0) | | | | (2735.0) | | | |
| Part II | | | | | | | | |
| Sugar Spheres (20/25 mesh) | 333.78 | 33.378 | 83.445 | 33.348 | 348.78 | 34.878 | 87.195 | 34.85 |
| Total | 1000.0 | 100 | 250.0 | | 1000.0 | 100 | 250.0 | |
| Talc, micronized | | | 0.225 | 0.0899 | | | 0.225 | 0.0899 |
| Total Fill Weight | | | 250.225 | | | | 250.225 | |

*Removed during processing

The in vitro drug release of the above formulation was evaluated in a 1000 mL purified water containing 0.05 M sodium lauryl sulfate using USP Apparatus II at 75 rpm. Table 11 summarizes the dissolution characteristics.

As seen in Table 11 below, the drug release rate of the formulations set forth in Table 10 is faster than the drug release rate of the branded product ANTARA®. Formulation #1000374, containing 2% sodium lauryl sulfate, releases 64% of the incorporated fenofibrate in 10 minutes; and substantially all of the incorporated fenofibrate in 30 minutes. ANTARA®, in contrast, releases 54% of the incorporated fenofibrate in 10 minutes; and 93% of the incorporated fenofibrate in 30 minutes. Formulation #1000375, containing 0.5% sodium lauryl sulfate, is more closely comparable to ANTARA® capsules, releasing 61% of the incorporated fenofibrate in 10 minutes; 94% of the incorporated fenofibrate in 30 minutes; and substantially all of the incorporated fenofibrate in 60 minutes.

TABLE 11

Fenofibrate Capsules USP, 130 mg
Dissolution Condition: USP Apparatus II, 75 rpm, 1000 mL, 0.05M SLS

| Product | 10 min | 15 min | 20 min | 30 min | 40 min | 60 min |
|---|---|---|---|---|---|---|
| ANTARA Capsules, 130 mg; B08003 | 54% | 74% | 84% | 93% | 97% | 100% |
| Fenofibrate Capsules, 130 mg #1000374 | 64% | 85% | 94% | 100% | 102% | 103% |
| Fenofibrate Capsules, 130 mg #1000375 | 61% | 77% | 86% | 94% | 98% | 102% |

Figure 2:
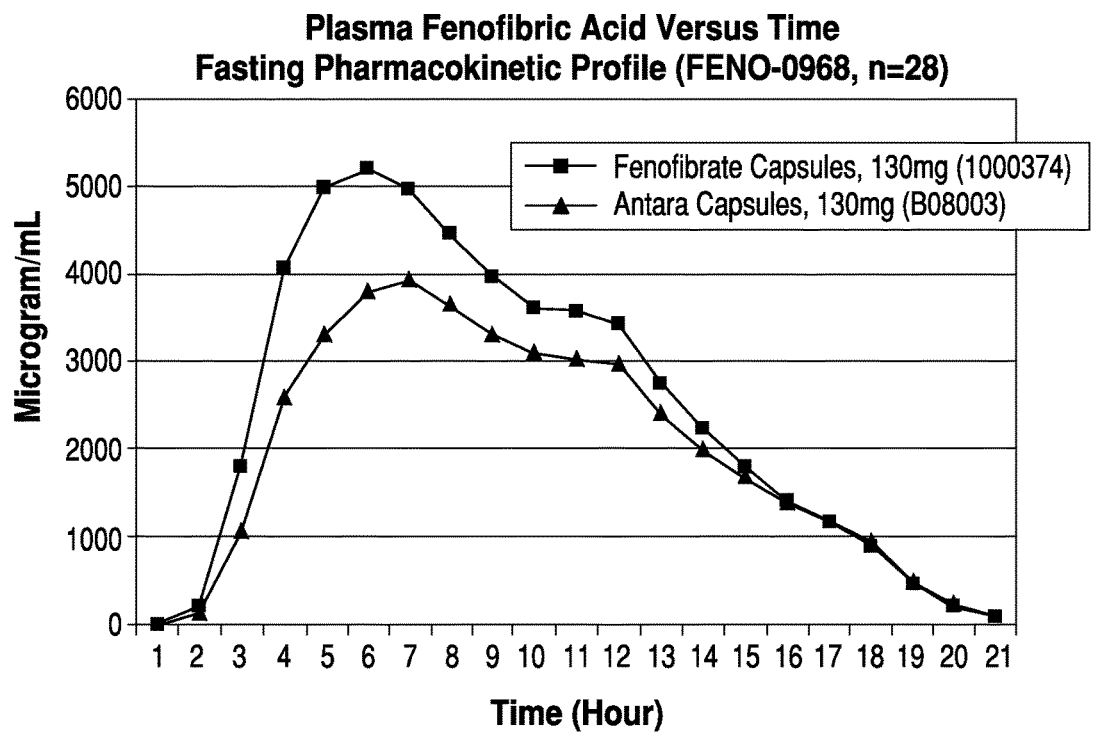
FIG. 2 and FIG. 3 show the concentration of fenofibrate in plasma over time upon administration of 130 mg ANTARA® capsules and administration of 130 mg capsules according to Example 4.
Figure 3:
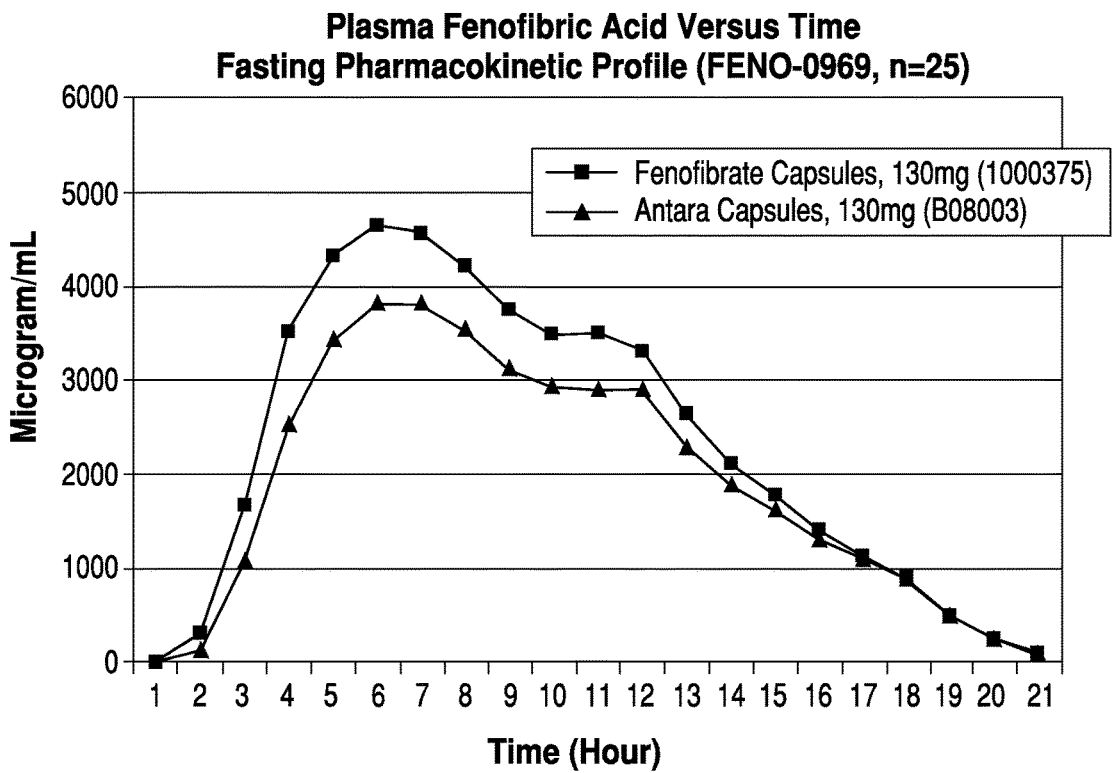

The above formulations were assessed against the reference listed drug product in two separate pilot bioequivalence studies versus ANTARA® 130 mg Capsules (B08003), under fasting conditions in open-label, single-dose, randomized, two-period, two-treatment crossover studies initiated with 28 normal healthy adult subjects each. The methodology was similar to the methodology used in Example 3. Summaries of the pharmacokinetic data from these studies are presented in Tables 12 and 13. FIGS. 2 and 3 present the pharmacokinetic profile of the formulations in Table 10.

TABLE 12

Fenofibrate Capsules USP, 130 mg
Pilot Bioequivalence Study Results - Fasting (n = 28) Conditions Study (FENO-0968)
(Formulation containing drug layered beads manufactured with 2% sodium lauryl sulfate, #20-#25 Sugar Spheres, Drug:Pharmacoat 603, 4:1)

| Lot # Brand | Fenofibric Acid - AUCL | | | | | Fenofibric Acid - CPEAK | | | | | Tpeak (hours) |
|---|---|---|---|---|---|---|---|---|---|---|---|
| | Mean (ng · hr/mL) | % CV | Ratio (M/I) | 90% CI | Intra subject % CV | Mean ng/mL | % CV | Ratio (M/I) | 90% CI | Intra subject % CV | |
| 1000374 | 125054 | 27.9 | 1.09 | 105-113 | 8% | 5428.7 | 35.3 | 1.28 | 119-138 | 16% | 4.0 (2-6) |
| B08003 | 114849 | 26.9 | | | | 4191.0 | 31.4 | | | | 5.0 (2-6) |

TABLE 13

Fenofibrate Capsules USP, 130 mg
Pilot Bioequivalence Study Results - Fasting (n = 25) Conditions Study (FENO-0969)
(Formulation containing drug layered beads manufactured with 0.5% sodium lauryl sulfate, #20-#25 Sugar Spheres, Drug:Pharmacoat 603, 4:1)

| Lot # Brand | Fenofibric Acid - AUCL | | | | | Fenofibric Acid - CPEAK | | | | | Tpeak (hours) |
|---|---|---|---|---|---|---|---|---|---|---|---|
| | Mean (ng · hr/mL) | % CV | Ratio (M/I) | 90% CI | Intra subject % CV | Mean ng/mL | % CV | Ratio (M/I) | 90% CI | Intra subject % CV | |
| 1000375 | 123828 | 35.8 | 1.12 | 107-117 | 9% | 4969 | 28.5 | 1.22 | 111-135 | 21% | 4.4 (2-9) |
| B08003 | 110477 | 33.6 | | | | 4099 | 34.8 | | | | 4.5 (2-10) |

The results of Table 12 indicate that Formulation #1000374, containing 2% sodium lauryl sulfate, exhibited a similar extent of absorption (AUCL) compared to ANTARA® capsules, but showed elevated drug concentration in the plasma. The 90% confidence interval for the AUCL is 105-113%, which falls within the FDA's desired confidence interval ratio of 80%-125%. However, the Cmax parameter for Formulation #1000374 has a 90% confidence interval of 119-138%. This result falls outside the FDA's desired confidence interval ratio of 80%-125%.

The results of Table 13 indicate that the Formulation #1000375, containing 0.5% sodium lauryl sulfate, also exhibited elevated drug concentration in the plasma, compared to ANTARA® capsules. The 90% confidence interval for the Cmax parameter for Formulation #1000375 has a 90% confidence interval of 111-135%, falling outside the FDA's desired confidence interval ratio of 80%-125%.

The pharmacokinetic results presented in the above table show that these modified formulations (containing 20-25 mesh sugar spheres as inert cores and 0.5 to 2% sodium lauryl sulfate) showed higher bioavailability than the reference product ANTARA®.

The beads prepared in the formulations of Example 4 are not suitable for use as the only beads in a formulation which is intended to be bioequivalent to ANTARA® capsules. However, the beads prepared in this formulation may be combined with slow beads, and used as fast beads in a formulation which is bioequivalent to ANTARA® capsules. Alternatively, the beads prepared in this formulation may be used as the only beads in a formulation which has a greater bioavailability than ANTARA® capsules.

Example 5

On the basis of the bioavailability study results of Examples 3 and 4, sodium lauryl sulfate was removed from the formulation and the effect of three different binder concentrations of Pharmacoat 603 (4.3% w/w, 6.5% w/w and 13.0% w/w) on the drug release was evaluated. A drug suspension containing micronized fenofibrate, HPMC (hypromellose, Pharmacoat 603), and the antifoaming agent simethicone was prepared in purified water, and sprayed onto 20-25 mesh sugar spheres in a fluid bed dryer (GPCG 3) equipped with a rotor granulator insert to produce the drug layered intermediate beads. The amount of fenofibrate was held constant at 130 mg/capsule, while the ratio of fenofibrate was varied between 4:1 and 12:1, as seen in Table 14.

TABLE 14

Fenofibrate Capsules USP, 130 mg
(Formulation composition without sodium lauryl sulfate)

|  | X07-047-81A1 4:1 Drug:Pharmacoat 603 ratio, 13% Pharmacoat 603 | | X07-047-82A1 8:1, Drug:Pharmacoat 603 ratio, 6.5% Pharmacoat 603 | | X07-047-83A1 12:1, Drug:Pharmacoat 603 ratio, 4.3% Pharmacoat 603 | |
|---|---|---|---|---|---|---|
|  | mg | % | mg | % | mg | % |
| Part I | | | | | | |
| Sugar Spheres (#20-#25) | 87.5 | 35.0 | 103.75 | 41.5 | 109.2 | 43.7 |
| Part II | | | | | | |
| Fenofibrate (Micronized) | 130.0 | 52.0 | 130.0 | 52.0 | 130.0 | 52.0 |
| Pharmacoat 603 (Hypromellose) | 32.5 | 13.0 | 16.25 | 6.5 | 10.8 | 4.3 |
| Purified Water* | (682.0) | | (682.0) | | (682.0) | |
| Total | 250.0 | | 250.0 | | 250.0 | |

*Removed during processing

The in vitro drug release of the formulations of Table 14 was evaluated in a 1000 mL purified water containing 0.025 M sodium lauryl sulfate using USP Apparatus II at 75 rpm. Table 15 summarizes the drug release characteristics, as seen in Table 15.

TABLE 15

Fenofibrate Capsules USP, 130 mg
Dissolution Condition: USP Apparatus II, 75 rpm, 1000 mL, 0.025M SLS

| Product | Drug:HPMC ratio | % HPMC | 10 min | 15 min | 20 min | 30 min | 40 min | 60 min |
|---|---|---|---|---|---|---|---|---|
| ANTARA ® Capsules, 130 mg; B08003 | | | 35% | 52% | 62% | 74% | 83% | 92% |
| Fenofibrate Capsules, 130 mg #X07-047-81A1 | 4:1 | 13% w/w | 72% | 80% | 95% | 97% | 98% | 99% |
| Fenofibrate Capsules, 130 mg #X07-047-82A1 | 8:1 | 6.5% w/w | 51% | 68% | 77% | 85% | 89% | 94% |
| Fenofibrate Capsules, 130 mg #X07-047-83A1 | 12:1 | 4.3% w/w | 18% | 28% | 38% | 49% | 57% | 66% |

The data presented in the above shows that higher concentrations of HPMC yielded more rapid drug release in formulations containing no sodium lauryl sulfate.

Example 6

Fenofibrate Dosage Forms which are Less Bioavailable than ANTARA® Capsules

Formulation X07-047-82A1 containing 6.5% w/w Pharmacoat 603 with no sodium lauryl sulfate was manufactured in a large scale equipment as lot 1000442 using Size#0EL capsules shell and evaluated in a bioequivalence study versus ANTARA® capsules. Table 16 describes this formulation.

TABLE 16

Fenofibrate Capsules, 130 mg, #1000442
(Contains drug layered beads manufactured without sodium lauryl sulfate (SLS), #20-#25 Sugar Spheres, 8:1 Drug:Pharmacoat 603)

|  | Fenofibrate Intermediate Beads, R&D-I 2052, 8:1 Drug:Pharmacoat 603 | | Fenofibrate Capsules USP, 130 mg, #1000442 | |
|---|---|---|---|---|
|  | mg/g | % | mg/capsule | % |
| Part I-A (Drug Layer Suspension) | | | | |
| Fenofibrate Micronized | 520.0 | 52.0 | 130.0 | 51.95324 |
| Hypromellose 2910 (Pharmacoat 603) | 65.0 | 6.5 | 16.25 | 6.5 |
| Simethicone | 0.22 | 0.022 | 0.055 | 0.02198 |
| Purified Water* | (2735.0) | | | |
| Part-IB | | | | |
| Sugar Spheres (20/25 mesh) | 414.78 | 41.478 | 103.695 | 41.4407 |
| Total | 1000.0 | 100 | 250.0 | |
| Talc, micronized | | | 0.225 | 0.08991 |
| Total Fill Weight | | | 250.225 | 100.0 |

*Purified removed during processing

The in vitro drug release of the above formulation was evaluated in a 1000 mL purified water containing 0.05 M sodium lauryl sulfate using USP Apparatus II at 75 rpm. Table 17 below summarizes the drug release characteristics.

TABLE 17

Fenofibrate Capsules USP, 130 mg
Dissolution (USP Apparatus II, 75 rpm, 1000 mL, 0.05M SLS)

| Product | 10 min | 15 min | 20 min | 30 min | 40 min | 60 min |
|---|---|---|---|---|---|---|
| ANTARA ® Capsules, 130 mg; B08003 | 54% | 74% | 84% | 93% | 97% | 100% |
| Fenofibrate Capsules, 130 mg #1000442 | 14% | 23% | 35% | 62% | 78% | 88% |

Figure 4:
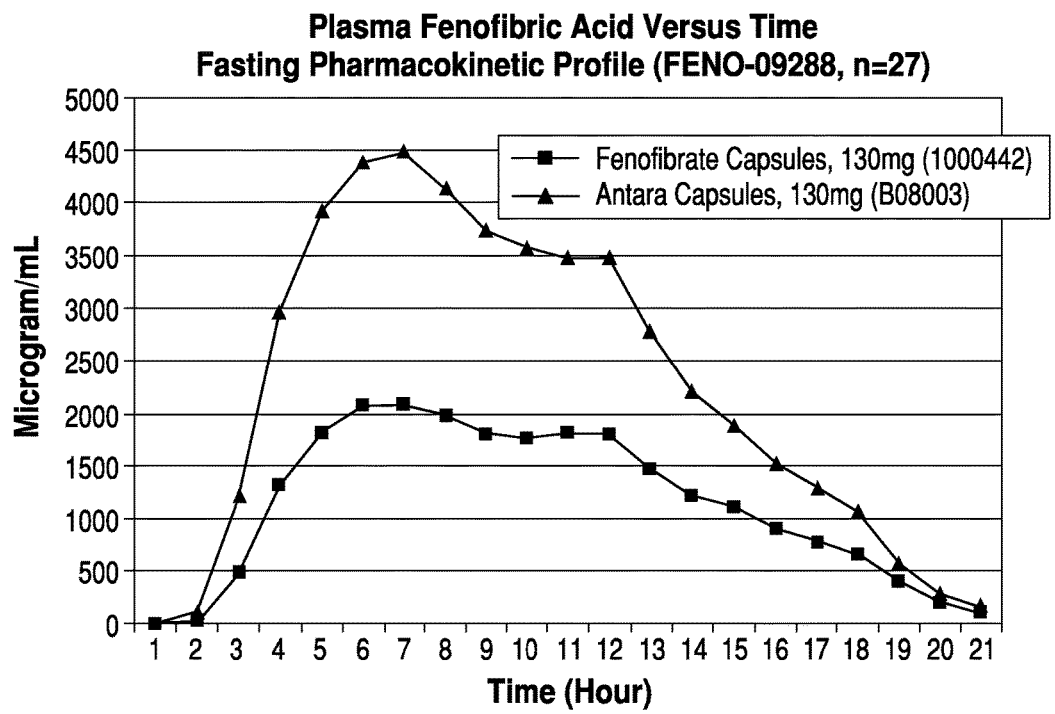
FIG. 4 shows the concentration of fenofibrate in plasma over time upon administration of 130 mg ANTARA capsules and administration of 130 mg capsules according to Example 6.

As seen in Table 17, the capsules of Table 16 release the drug more slowly than the comparative ANTARA® capsules. After 10 minutes, the comparative ANTARA® capsules released 54% of the drug, while the capsules of Table 14 released only 14% of the drug. Additionally, the capsules of Table 14 were assessed in a bioequivalence study versus ANTARA® Capsules, 130 mg in an open-label, single-dose, randomized, two-period, two-treatment crossover study using 32 normal healthy subjects (27 completed the study). The methodology was similar to the methodology used in Example 3. A summary of the pharmacokinetic data from this study is presented in Table 18. Also, a plot showing the pharmacokinetic profile of the capsules of Table 16 is shown in FIG. 4.

125%, and indicates that the capsules of Table 16 are not bioequivalent to ANTARA® capsules.

Example 7

Fenofibrate Dosage Forms which are Bioequivalent to ANTARA® Capsules

Three alternative intermediate bead formulations were scaled-up. The first group of beads, Fenofibrate Intermediate Beads, Type A, Lot#R&D-I2133, contain 0.5% sodium lauryl sulfate. The second group of beads, Fenofibrate Intermediate Beads, Type B, Lot#R&D-I2134, contain 2%

TABLE 18

Fenofibrate Capsules USP, 130 mg (Lot 1000442)
Pilot Bioequivalence Study Results - Fasting (n = 27) Conditions Study (FENO-09288)

| Lot #<br>Brand | Fenofibric Acid - AUCL | | | | | Fenofibric Acid - CPEAK | | | | | Tpeak*<br>(hours) |
|---|---|---|---|---|---|---|---|---|---|---|---|
| | Mean<br>(ng · hr/mL) | %<br>CV | Ratio<br>(M/I) | 90%<br>CI | Intra<br>subject<br>% CV | Mean<br>ng/mL | %<br>CV | Ratio<br>(M/I) | 90%<br>CI | Intra<br>subject<br>% CV | |
| 1000442 | 76734 | 40.0 | 0.56 | 53-59 | 13% | 2263.4 | 31.8 | 0.49 | 45-53 | 18.0% | 5.0<br>(3-10) |
| B08003 | 134952 | 34.9 | | | | 4748.7 | 36.8 | | | | 4.0<br>(2-6) |

*Median values presented (range of values)

The capsules of Table 16 exhibited poor bioavailability under fasting conditions due to a low AUCL and Cmax. The results of Table 18 indicate that the capsules of Table 16, containing fenofibrate and HPMC in a ratio of 8:1 and no sodium lauryl sulfate, exhibited low absorption (AUCL) compared to ANTARA® capsules. The capsules of Table 16 showed between 53% and 59% of the absorption (AUCL) observed with the branded product, with a confidence interval of 90%. Additionally, the Cmax parameter for capsules of Table 16 has a 90% confidence interval of 45% to 53% when compared to the branded product. This result falls outside the FDA's desired confidence interval ratio of 80%- sodium lauryl sulfate. The third group of beads, Fenofibrate Intermediate Beads, Type C, Lot# R&D-I2128, contains no sodium lauryl sulfate.

Based on pharmacokinetic analysis, two capsule formulations containing different ratios of the above beads were machine encapsulated in size#0EL and dosed in a bioequivalence study. The first capsule formulation, lot #1000529, contained an 80:20 ratio of Type A beads and Type C beads, and the second capsule formulation, lot #1000530, contained a 75:25 ratio of Type B and Type C beads. Tables 19, 20, and 21 summarize these two capsule formulations and drug release characteristics.

TABLE 19

Fenofibrate Capsules USP, 130 mg, #1000529
(Contains 80% w/w Fenofibrate Intermediate Beads, Type A (0.5% SLS), Lot# R&D-I12133,
and 20% w/w Fenofibrate Intermediate Beads, Type C (No SLS), Lot# R&D-I12128)

| | Fenofibrate<br>Intermediate Beads<br>Type A, 0.5% SLS,<br>R&D-I2133<br>Drug:HPMC, 4:1 | | Fenofibrate<br>Intermediate Beads<br>Type C, No SLS,<br>R&D-I2128,<br>Drug:HPMC, 8:1 | | 80% w/w<br>Type A<br>Beads | 20% w/w<br>Type C<br>Beads | Fenofibrate<br>Capsules USP,<br>130 mg,<br>#1000529<br>80:20 | |
|---|---|---|---|---|---|---|---|---|
| | mg/g | % | mg/g | % | Mg | mg | mg | % |
| Part I-A (Drug<br>Layer Suspension) | | | | | | | | |
| Fenofibrate<br>Micronized | 520.0 | 52.0 | 520.0 | 52.0 | 104.0 | 26.0 | 130.0 | 51.95 |
| Hypromellose 2910<br>(Pharmacoat 603) | 126.0 | 12.6 | 65.0 | 6.5 | 25.2 | 3.25 | 28.45 | 11.37 |
| Sodium Lauryl Sulfate | 5.0 | 0.5 | | | 1.0 | | 1.0 | 0.4 |
| Simethicone | 0.22 | 0.022 | 0.22 | 0.022 | 0.044 | 0.011 | 0.055 | 0.022 |
| Purified Water* | (2735.0) | | (2735.0) | | | | | |

TABLE 19-continued

Fenofibrate Capsules USP, 130 mg, #1000529
(Contains 80% w/w Fenofibrate Intermediate Beads, Type A (0.5% SLS), Lot# R&D-I12133,
and 20% w/w Fenofibrate Intermediate Beads, Type C (No SLS), Lot# R&D-I12128)

|  | Fenofibrate Intermediate Beads Type A, 0.5% SLS, R&D-I2133 Drug:HPMC, 4:1 | | Fenofibrate Intermediate Beads Type C, No SLS, R&D-I2128, Drug:HPMC, 8:1 | | 80% w/w Type A Beads | 20% w/w Type C Beads | Fenofibrate Capsules USP, 130 mg, #1000529 80:20 | |
|---|---|---|---|---|---|---|---|---|
|  | mg/g | % | mg/g | % | Mg | mg | mg | % |
| Part-IB |  |  |  |  |  |  |  |  |
| Sugar Spheres (20/25 mesh) | 348.78 | 34.878 | 414.78 | 41.48 | 69.756 | 20.739 | 90.495 | 36.17 |
| Total | 1000.0 | 100 | 1000.0 | 100 | 200.0 | 50.0 | 250.0 |  |
| Talc, micronized |  |  |  |  | 0.225 | — | 0.225 | 0.09 |
| Total Capsule Fill Wt. |  |  |  |  |  |  | 250.225 |  |

*Removed during processing

TABLE 20

Fenofibrate Capsules USP, 130 mg, #1000530
(Contains 75% w/w Fenofibrate Intermediate Beads, Type B (2% SLS), Lot#R&D-I2134
and 25% w/w Fenofibrate Intermediate Beads, Type C (No SLS), Lot# R&D-I2128)

|  | Fenofibrate Intermediate Beads Type B, 2% SLS, Drug:Pharmacoat, 4:1, R&D-I2134 | | Fenofibrate Intermediate Beads Type C, R&D-I2128, No SLS Drug:HPMC, 8:1 | | 75% w/w Type B Beads | 25% w/w Type C Beads | Fenofibrate Capsules USP, 130 mg, #1000530 75:25 | |
|---|---|---|---|---|---|---|---|---|
|  | mg/g | % | mg/g | % | mg | mg | mg | % |
| Part I (Drug Layer Suspension) |  |  |  |  |  |  |  |  |
| Fenofibrate Micronized | 520.0 | 52.0 | 520.0 | 52.0 | 97.5 | 32.5 | 130.0 | 51.95 |
| Hypromellose 2910 (Pharmacoat 603) | 126.0 | 12.6 | 65.0 | 6.5 | 23.625 | 4.0625 | 27.6875 | 11.07 |
| Sodium Lauryl Sulfate | 20.0 | 2.0 | NA | NA | 3.75 |  | 3.75 | 1.5 |
| Simethicone | 0.22 | 0.022 | 0.22 | 0.022 | 0.04125 | 0.01375 | 0.055 | 0.22 |
| Purified Water* | (2735.0) | (2735.0) | (2735.0) |  |  |  |  |  |
| Part II |  |  |  |  |  |  |  |  |
| Sugar Spheres (20/25 mesh) | 333.78 | 33.38 | 414.78 | 41.478 | 62.58375 | 25.92375 | 88.5075 | 35.37 |
| Total | 1000.0 | 1000.0 | 1000.0 | 100 | 187.5 | 62.5 | 250.0 |  |
| Talc, micronized |  |  |  |  | 0.225 |  | 0.225 | 0.09 |
| Total Capsule Fill Wt, mg |  |  |  |  |  |  | 250.225 |  |

*Removed during processing

The drug release characteristics of the above two capsule formulations are evaluated using USP Apparatus II, 75 rpm, 1000 mL, 0.05 M SLS, and are summarized in Table 21. As seen in Table 21, the dissolution rate of the capsule formulations of Tables 19 and 20 is slower than the dissolution rate of ANTARA® capsules containing an equivalent amount of fenofibrate, i.e., 130 mg. Additionally, the drug release rate of the capsule formulations of Tables 19 and 20 is slower than a capsule prepared using the formulation of Table 14, containing fenofibrate and HPMC in a ratio of 8:1, with no sodium lauryl sulfate. The dissolution rate of the capsule formulations of Tables 19 and 20 is also substantially slower than a capsule prepared using Type B beads alone, where the Type B beads contain fenofibrate and HPMC in a ratio of 4.1:1, with 2% sodium lauryl sulfate.

TABLE 21

Fenofibrate Capsules USP, 130 mg
Dissolution Condition: USP Apparatus II, 75 rpm, 1000 mL, 0.05M SLS

| Product | 10 min | 15 min | 20 min | 30 min | 40 min | 60 min |
|---|---|---|---|---|---|---|
| ANTARA Capsules, 130 mg; B08017 | 49% | 73% | 84% | 94% | 97% | 100% |
| Fenofibrate Intermediate Beads, R&D I2052, Type C Beads | 63% | 78% | 84% | 90% | 93% | 97% |

TABLE 21-continued

Fenofibrate Capsules USP, 130 mg
Dissolution Condition: USP Apparatus II, 75 rpm, 1000 mL, 0.05M SLS

| Product | 10 min | 15 min | 20 min | 30 min | 40 min | 60 min |
|---|---|---|---|---|---|---|
| Fenofibrate Intermediate Beads, R&D I2134, Type B Beads | 92% | 98% | 100% | 100% | 100% | 100% |
| Fenofibrate Capsule, 130 mg, Lot. 1000529 | 33% | 50% | 64% | 79% | 88% | 96% |
| Fenofibrate Capsule, 130 mg, Lot. 1000530 | 45% | 60% | 68% | 78% | 85% | 93% |

Figure 5:
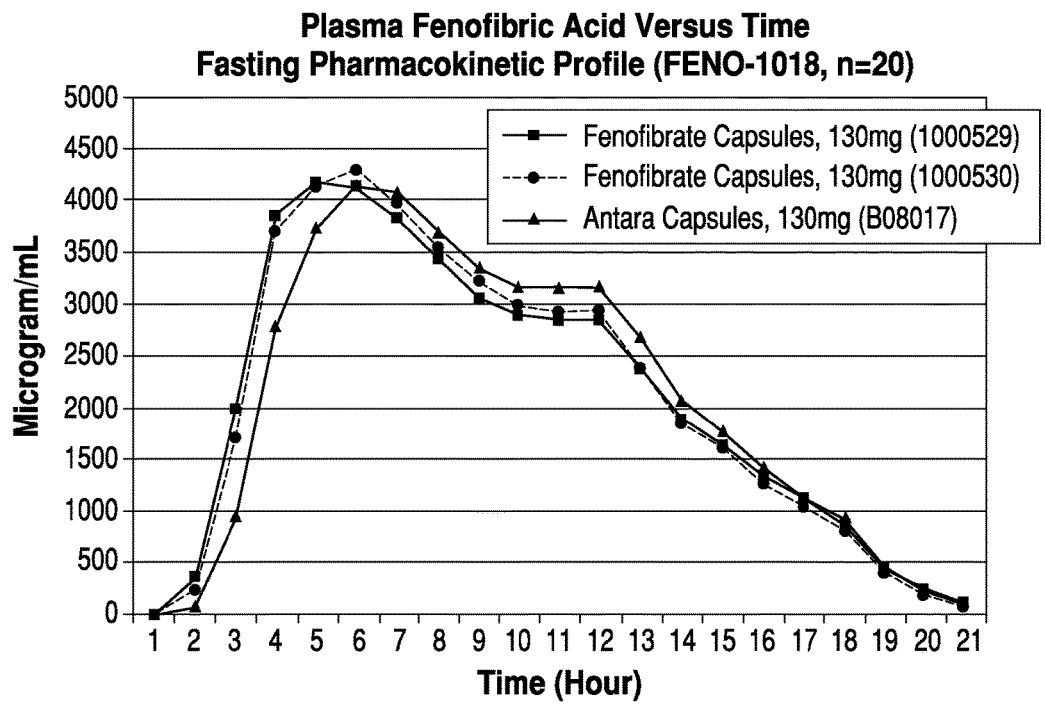
FIG. 5 shows the concentration of fenofibrate in plasma over time upon administration of 130 mg ANTARA® capsules and administration of 130 mg capsules according to Example 7.

The capsules of Tables 19 and 20 were assessed in a bioequivalence study versus ANTARA® Capsules, 130 mg, in an open-label, single-dose, randomized, two-period, two-treatment crossover study using 21 normal healthy subjects. The methodology was similar to the methodology used in Example 3. A summary of the pharmacokinetic data from this study is presented in Table 22. A plot showing pharmacokinetic profile, specifically plasma levels, is shown in FIG. 5.

TABLE 22

Fenofibrate Capsules USP, 130 mg
Pilot Bioequivalence Study Results - Fasting
(n = 21) Conditions; Study (FENO-1018)
Treatment A: Lot 1000529 contains 80% Fast Beads (0.5% SLS) and 20% Slow Beads (No SLS); Dose: 1 × 130 mg
Treatment B: Lot 1000530 contains 75% Fast Beads (2% SLS) and 25% Slow Beads (No SLS); Dose: 1 × 130 mg
Treatment C: ANTARA ® Capsules, Lot: B08017; Dose: 1 × 130 mg; Oscient/Lupin

| | Mean | Mean | 90% CI |
|---|---|---|---|
| | Treatment A = Lot 1000529 | Treatment C = Lot B08017 | |
| AUCI (ng · hr/mL) | 122189.62 | 124010.37 | 94-106 |
| AUCL(ng · hr/mL) | 113485.24 | 117167.45 | 92-105 |
| CPEAK (ng/mL) | 4498.10 | 4720.35 | 88-108 |
| TPEAK (Hour)* | 3.5 (2-10) | 4 (2-12) | |
| | Treatment B = Lot 1000530 | Treatment C = Lot B08017 | |
| AUCI (ng · hr/mL) | 116320.92 | 124010.37 | 90-102 |
| AUCL(ng · hr/mL) | 108823.93 | 117167.45 | 89-101 |
| CPEAK (ng/mL) | 4656.90 | 4720.35 | 90-109 |
| TPEAK (Hour)* | 4.0 (2.0-24) | 4 (2-12) | |

*Median values, with range in parentheses.

The pharmacokinetic results presented in Table 22 demonstrate that the formulations of Tables 19 and 20 were each bioequivalent to ANTARA®. Formulation #1000529, containing 80% Type A beads and 20% Type C beads, exhibited an extent of absorption (AUCL) which was between 92% and 105% of the absorption observed with ANTARA® capsules, within a confidence interval of 90%. Formulation #1000530, containing 75% Type B beads and 25% Type C beads, exhibited an extent of absorption (AUCL) which was between 89% and 101% of the absorption observed with ANTARA® capsules, within a confidence interval of 90%. This result falls within the FDA's desired confidence interval ratio of 80%-125%.

Additionally, the Cmax parameter for Formulation #1000529 was 88% to 108% of the Cmax observed with ANTARA® capsules, within a confidence interval of 90%; and the Cmax parameter for Formulation #1000530 was 90% to 109% of the Cmax observed with ANTARA® capsules, within a confidence interval of 90%. This result falls within the FDA's desired confidence interval ratio of 80%-125%. The results of Table 22 indicate that the Formulation #1000529 and Formulation #1000530 are each bioequivalent to ANTARA® capsules.

Example 8

Fenofibrate Dosage Forms which are Bioequivalent to ANTARA® Capsules

A large scale batch, Formulation#1000596 was manufactured using the Formulation composition of 1000530 (shown in Table 20). This capsule contains two different types of Fenofibrate Intermediate Beads, one containing no surfactant (Fenofibrate Intermediate Beads, Type C, 520 mg/g) and the other containing sodium lauryl sulfate as a surfactant (Fenofibrate Intermediate Beads, Type B). Each capsule contains 25% w/w Fenofibrate Intermediate Beads Type C (520 mg/g) and 75% w/w Fenofibrate Intermediate Beads Type B which corresponds to theoretical fill weights of 62.5 mg and 187.725 mg, respectively. The actual fill weight of each bead is adjusted based on the potency factor assigned to each bead prior to encapsulation. Each bead type was filled into the capsule shell using a separate dosing station during encapsulation.

Figure 6:
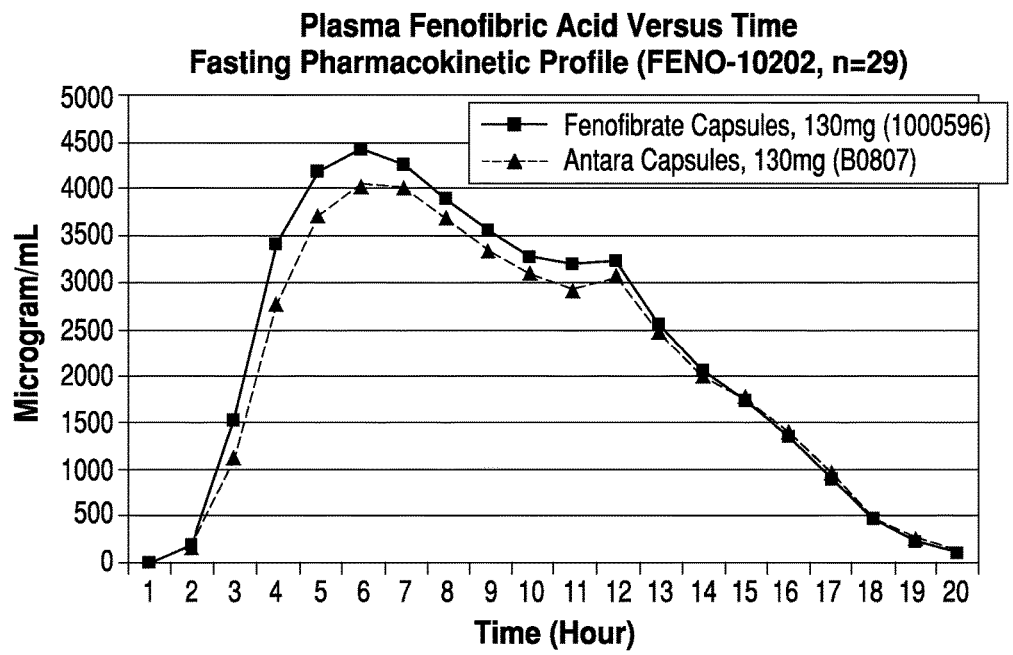
FIG. 6 and FIG. 7 show the concentration of fenofibrate in plasma over time upon administration of 130 mg ANTARA® capsules and administration of 130 mg capsules according to Example 8.
Figure 7:
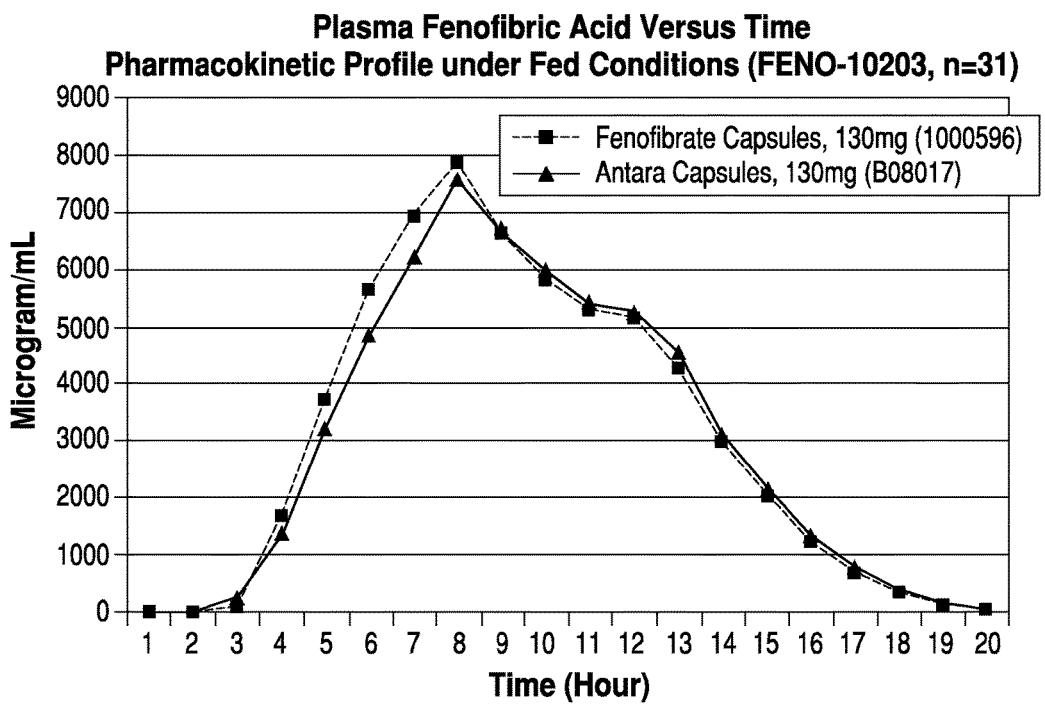

The resulting Capsules USP, 130 mg (Lot. 100596) were dosed in a bioequivalence study versus the reference listed drug, ANTARA® Capsules, 130 mg. The study was a single dose, open label, randomized, 2-period, 2-treatment crossover of the test and reference products administered under fasting and post-prandial conditions. Statistical analyses of the data revealed that the 90% confidence intervals were within the acceptable bioequivalent range of 80% and 125% for the natural log transformed parameters AUCL, AUCI, and CPEAK for fenofibric acid. This study demonstrates that Capsules of Lot. 100596, 130 mg are bioequivalent to ANTARA® Capsules, 130 mg, following a single, oral 130 mg (1×130 mg capsule) dose administered under fasting and post-prandial conditions. A summary of the pharmacokinetic data from this study is presented in Table 23 and Table 24. FIG. 6 and FIG. 7 display the pharmacokinetic profile, specifically plasma concentration of fenofibrate over time, for Capsules of Lot. 100596, 130 mg, which are bioequivalent to ANTARA® Capsules, 130 mg.

TABLE 23

Fenofibrate Capsules USP, 130 mg (Lot#1000596)
Bioequivalence Study Results - Fasting (n = 29) Conditions; Study (FENO-10202)
(Formulation 1000596 contains 75% Fast Beads (2% SLS Beads) and 25% Slow Beads (No SLS))

| | Fenofibric Acid - AUCL | | | | | Fenofibric Acid - CPEAK | | | | | |
|---|---|---|---|---|---|---|---|---|---|---|---|
| Lot # | Mean (ng·hr/mL) | % CV | Ratio (M/I) | 90% CI | Intra subject % CV | Mean ng/mL | % CV | Ratio (M/I) | 90% CI | Intra subject % CV | Tpeak (hours) |
| 1000596 | 121033 | 36.5 | 0.97 | 92-102 | 11.5% | 4617 | 35.0 | 1.08 | 99-117 | 19% | 4.2 (2-10) |
| B08017 | 123562 | 34.4 | | | | 4321 | 39.4 | | | | 4.5 (2-10) |

TABLE 24

Fenofibrate Capsules USP, 130 mg (Lot#1000596)
Bioequivalence Study Results - Fed (Post-Prandial) (n = 31) Conditions; Study (FENO-10203)
(Formulation 1000596 contains 75% Fast Beads (2% SLS Beads) and 25% Slow Beads (No SLS))

| | Fenofibric Acid - AUCL | | | | | Fenofibric Acid - CPEAK | | | | | |
|---|---|---|---|---|---|---|---|---|---|---|---|
| Lot # | Mean (ng·hr/mL) | % CV | Ratio (M/I) | 90% CI | Intra subject % CV | Mean ng/mL | % CV | Ratio (M/I) | 90% CI | Intra subject % CV | Tpeak (hours) |
| 1000596 | 140411 | 31.6 | 0.97 | 94-100 | 7.22% | 8300 | 17.8 | 1.00 | 96-104 | 10% | 5.7 (3-12) |
| B08017 | 145211 | 32.0 | | | | 8381 | 20.6 | | | | 6.1 (2-12) |

4. Comparative Example

The Comparative Example presented herein is drawn from U.S. Pat. No. 7,863,331.

Example 4 of U.S. Pat. No. 7,863,331 presents a formulation comprising inert cores coated with a layer of fenofibrate, HPMC, and SLS, as presented in Table 25 below.

TABLE 25

Fenofibrate Capsules USP, Prepared according to Example 4 of U.S. Pat. No. 7,863,331

| FORMULA | PERCENTAGE BY MASS |
|---|---|
| Neutral cores | 16.44 |
| Micronized fenofibrate | 63.69 |
| Hydroxypropylmethyl cellulose 3.0 Viscosity cP | 12.04 |
| Sodium lauryl sulfate | 3.25 |
| Dimethicone | 0.25 |
| Simethicone | 0.03 |
| Talc | 0.63 |
| Outer layer | |
| Hydroxypropylmethyl cellulose 6.0 Viscosity cP | 2.57 |
| Talc | 1.1 |

Example 6 of U.S. Pat. No. 7,863,331 presents bioavailability data for a 130 mg fenofibrate capsule prepared according to the formulation of Table 25. The 130 mg capsule has a Cmax in the fasted state of 4375 ng/mL. These results are compared to the results obtained with various exemplary embodiments described herein in Table 26.

TABLE 26

Fenofibrate Capsules USP, 130 mg Bioequivalence Data

| Lot # | Fenofibric Acid-AUCL Mean (ng · hr/mL) | Fenofibric Acid-Cmax Mean (ng/mL) |
|---|---|---|
| B08017 (ANTARA ®)[a] | 123455 | 4321 |
| Example 6, U.S. Pat. No. 7,863,331 | 114853 | 4375 |
| 1000317[b] | 141825 | 6549 |
| 1000374[c] | 125054 | 5428.7 |
| 1000375[d] | 123828 | 4969 |

[a]See Table 23.
[b]See Table 9; capsules containing beads with 28.9% fenofibrate, as disclosed herein.
[c]See Table 12; capsules containing beads with 52% fenofibrate, as disclosed herein.
[d]See Table 13; capsules containing beads with 52% fenofibrate, as disclosed herein.

Thus, Table 26 compares results obtained with the prior art products to capsules containing fenofibrate beads or granules disclosed herein. The granules disclosed herein comprise fenofibrate; from 0.5% to 2% by weight of a surfactant; and from about 5% to about 15% by weight of a water soluble or water dispersible cellulosic binder. The mass ratio of the drug to the binder in the dosage forms disclosed herein and listed in Table 26 (Lot #1000317, Lot #1000374, and Lot #1000375) is about 4:1 to about 4.15. The prior art granules described in Example 6 of U.S. Pat. No. 7,863,331 comprise fenofibrate; 3.25% by weight of a surfactant; and about 12% by weight of a water soluble or water dispersible cellulosic binder. The mass ratio of the drug to the binder in the dosage form described in Example 6 of U.S. Pat. No. 7,863,331 is 5.29. As seen in Table 26, reducing the mass ratio of the drug to the binder from 5.29 to about 4.1 to about 4.15 significantly increases bioavailability, seen as an increase in Cmax.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A dosage form comprising a plurality of beads or particles, each of said beads or particles comprising:
   from 25% to 55% by weight of a drug selected from the group consisting of fenofibric acid, pharmaceutically acceptable salts thereof, pharmaceutically acceptable esters thereof, and prodrugs thereof, substantially all of said drug being incorporated in said plurality of beads or particles;
   an effective amount of a surfactant; and
   from about 5% to about 15% by weight of a water soluble or water dispersible cellulosic binder;
   wherein the mass ratio of said drug to said binder in said dosage form is between about 3.5:1and 4.5:1.

2. The dosage form according to claim 1, wherein each of said beads or particles comprises an inert core; and a pharmaceutical composition comprising said drug, said surfactant; and said cellulosic binder;
   wherein said pharmaceutical composition is coated on said inert core.

3. The dosage form according to claim 1, wherein:
   each of said beads or particles comprises 45% to about 55% by weight of said drug.

4. The dosage form according to claim 1, wherein:
   each of said beads or particles comprises 25% to about 35% by weight of said drug.

5. The dosage form according to claim 3, wherein:
   said dosage form comprises 40 to 200 mg fenofibrate.

6. The dosage form according to claim 3, wherein:
   said dosage form and said comparative dosage form each comprise 40 to 200 mg fenofibrate.

7. A dosage form comprising a plurality of beads or particles, said beads or particles each comprising a pharmaceutical composition comprising:
   from about 20% to about 55% by weight of said beads or particles of a micronized drug selected from the group consisting of fenofibric acid, pharmaceutically acceptable salts thereof, pharmaceutically acceptable esters thereof, and prodrugs thereof;
   from 0.3% to 10% by weight of said beads or particles of a surfactant; and
   from about 5% to about 15% by weight of said beads or particles of a water soluble or water dispersible cellulosic binder.

8. The dosage form according to claim 7, wherein:
   said pharmaceutical composition comprises 45% to about 55% by weight of said drug.

9. The dosage form according to claim 7, wherein:
   said pharmaceutical composition comprises 25% to about 35% by weight of said drug.

10. The dosage form according to claim 7, wherein:
    said dosage form comprises 40 to 200 mg fenofibrate.

11. A dosage form comprising a plurality of beads or particles, said beads or particles each comprising an inert core with a particle size of 20 to 50 mesh and a pharmaceutical composition coated on said inert core;
    said pharmaceutical composition comprising:
    from about 20% to about 55% by weight of a drug selected from the group consisting of fenofibric acid, pharmaceutically acceptable salts thereof, pharmaceutically acceptable esters thereof, and prodrugs thereof;
    from 0.3% to 10% by weight of said beads or particles of a surfactant; and
    from about 5% to about 15% by weight of a water soluble or water dispersible cellulosic binder;
    wherein the mass ratio of said drug to said binder in said dosage form is between about 3.5:1and 4.5:1.

12. A method of reducing a cholesterol level and/or increasing high-density lipoprotein levels in a patient at risk of cardiovascular disease, comprising administering a dosage form to said patient;
    said dosage form comprising a plurality of beads or particles, said beads or particles each comprising:
    from 20% to 55% by weight of a drug selected from the group consisting of fenofibric acid, pharmaceutically acceptable salts thereof, pharmaceutically acceptable esters thereof, and prodrugs thereof;
    from 0.3% to 10% by weight of a surfactant; and
    from 5% to 15% by weight of a water soluble or water dispersible cellulosic binder;
    wherein the mass ratio of said drug to said binder in said dosage form is between 3.5:1 and 4.5:1.

13. The method of claim 12, wherein said dosage form is administered in conjunction with a statin.

14. The dosage form according to claim 11, wherein said dosage form is further characterized by least one of the following conditions:
    a) said drug is micronized; and
    b) said surfactant is present in an amount of between about 0.5% by weight and about 5% by weight.

15. The dosage form according to claim 14, wherein said dosage form is further characterized in that said inert core has a mesh size of 20 to 25 mesh; and
    said surfactant is present in an amount of between about 0.5% by weight and about 3% by weight.

16. The dosage form according to claim 14, wherein said dosage form is further characterized in that said inert core has a mesh size of 35 to 45 mesh; and
    said surfactant is present in an amount of between about 0.5% by weight and about 3% by weight.

17. The dosage form according to claim 14, wherein:
    said micronized drug has a weight average particle size of between 1 and 15 microns, or
    said micronized drug has a particle size range such that at least 99% of drug particles have a particle size of <50 microns; at least 90% of drug particles have a particle size of <15 microns; and no more than 10% of drug particles have a particle size of <1 micron.

18. The method according to claim 12, wherein said dosage form is further characterized by least one of the following conditions:
    a) said drug is micronized; and
    b) said surfactant is present in an amount of between about 0.5% by weight and about 5% by weight.

19. The method according to claim 12, wherein said dosage form is further characterized in that said beads or particles each comprise an inert core with a particle size of 20 to 50 mesh, said pharmaceutical composition being coated on said inert core.

20. The method according to claim 18, wherein said an inert core has a particle size of 20 to 25 mesh.

21. The method according to claim 18, wherein said an inert core has a particle size of 35 to 45 mesh.

22. The dosage form according to claim 11, wherein the dosage form comprises the plurality of beads or particles, each bead or particle consisting of the inert core and the pharmaceutical composition coated on the inert core.

* * * * *